(12) United States Patent
Hermel-Davidock et al.

(10) Patent No.: US 11,198,801 B2
(45) Date of Patent: *Dec. 14, 2021

(54) AMPHIPHILIC GRAFT COPOLYMERS AND MEDICAL DEVICES WITH ENHANCED BOND STRENGTH

(71) Applicant: Becton, Dickinson and Company, Franklin Lakes, NJ (US)

(72) Inventors: Theresa Hermel-Davidock, Vernon Hills, IL (US); Tea Datashvili, Hackensack, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 515 days.

This patent is subject to a terminal disclaimer.

(21) Appl. No.: 16/104,425

(22) Filed: Aug. 17, 2018

(65) Prior Publication Data

US 2019/0055436 A1    Feb. 21, 2019

Related U.S. Application Data

(60) Provisional application No. 62/547,167, filed on Aug. 18, 2017, provisional application No. 62/684,946, filed on Jun. 14, 2018.

(51) Int. Cl.

| | | |
|---|---|---|
| *C09J 123/12* | (2006.01) |
| *C08F 292/00* | (2006.01) |
| *C09J 11/08* | (2006.01) |
| *C09J 5/00* | (2006.01) |
| *C08L 23/12* | (2006.01) |
| *C08F 255/02* | (2006.01) |
| *A61L 29/04* | (2006.01) |
| *A61M 39/10* | (2006.01) |
| *C09J 5/06* | (2006.01) |
| *C09C 1/30* | (2006.01) |
| *C08L 51/06* | (2006.01) |
| *C08K 9/06* | (2006.01) |
| *C08F 230/08* | (2006.01) |

(52) U.S. Cl.
CPC ........... *C09J 123/12* (2013.01); *A61L 29/041* (2013.01); *A61M 39/10* (2013.01); *C08F 255/02* (2013.01); *C08F 292/00* (2013.01); *C08L 23/12* (2013.01); *C09J 5/00* (2013.01); *C09J 5/06* (2013.01); *C09J 11/08* (2013.01); *A61M 2207/00* (2013.01); *C08F 230/08* (2013.01); *C08K 9/06* (2013.01); *C08L 51/06* (2013.01); *C09C 1/309* (2013.01)

(58) Field of Classification Search
CPC ............................ C08F 255/02; C08F 292/00
See application file for complete search history.

(56) References Cited

U.S. PATENT DOCUMENTS

| | | |
|---|---|---|
| 4,959,406 A | 9/1990 | Foltin et al. |
| 5,735,830 A | 4/1998 | Fritz et al. |
| 5,910,523 A | 6/1999 | Hudson |
| 8,911,658 B2 | 12/2014 | Jiang |
| 2003/0018306 A1 | 1/2003 | Bucay-Couto et al. |
| 2004/0071994 A1 | 4/2004 | Busch et al. |
| 2007/0244284 A1 | 10/2007 | Cheng et al. |
| 2009/0149614 A1* | 6/2009 | Loyens .................. H01B 3/441 526/172 |

FOREIGN PATENT DOCUMENTS

| | | | |
|---|---|---|---|
| CN | 105778295 A | * | 7/2016 |
| CN | 106674750 A | | 5/2017 |
| WO | 2008027720 A2 | | 3/2008 |

OTHER PUBLICATIONS

Morawski et al. (The effect of elastomer type and molding conditions on the properties of TPO blends (Year: 1997).*
Machine translation of CN-105778295-A (Year: 2016).*
PCT International Search Report and Written Opinion in PCT/US2018/046941, dated Dec. 7, 2018, 15 pages.
PCT International Search Report and Written Opinion in PCT/US2018/046948, dated Dec. 7, 2018, 16 pages.
PCT International Search Report and Written Opinion PCT/US2018/046946, dated Dec. 7, 2018, 17 pages.
Bailly, Mathieu , et al., "Preparation and characterization of thermoplastic olefin/nanosilica composites using a silane-grafted polypropylene matrix", Elsevier Ltd., Mar. 20, 2009, 2472-2480.
Bauer, Frank, et al., "Preparation of Scratch and Abrasion Resistant Polymeric Nanocomposites by Monomer Grafting onto Nanoparticles, 3a Effect of Filler Particles and Grafting Agents", Macromolecular Materials and Engineering, Jan. 22, 2002, 546-552.
Hasse, Andre , et al., "Reinforcement of Silica-Filled EPM Compounds using Vinylsilanes", Applied Technology Advanced Fillers, 1-6.

(Continued)

*Primary Examiner* — Wenwen Cai
(74) *Attorney, Agent, or Firm* — Servilla Whitney LLC

(57) ABSTRACT

Amphiphilic graft copolymers comprise a polypropylene backbone and hybrid micromolecule side-chains based on organo-functional silanes (PP-g-XSiOA) in the presence of a co-agent, for example, difunctional metallic diacrylate monomers, where "X" is an organic group or an organo-functional group, and "A" is a metal, an inorganic oxide, an inorganic hydroxide, or any other inorganic material. X may be derived from a compound selected from the group consisting of: epoxy, amino, acrylate, methacryloxy, and vinyl; and A is selected from the group consisting of: silicon, (Si), aluminum (Al), iron (Fe), titanium (Ti), silver (Ag), zinc (Zn), nickel (Ni), calcium (Ca), copper (Cu), tin (Sn); oxides thereof; hydroxides thereof; and mixtures of the foregoing. These copolymers are suitable for forming medical devices and/or as additives to base polymeric formulations for medical devices for improving laser marking, antimicrobial resistance, adhesive free bond strength, paintability and dyeability.

33 Claims, 15 Drawing Sheets

(56) References Cited

OTHER PUBLICATIONS

Sherman, Lilli Manolis, "Laser Marking Has a Bright Future in Plastics", Plastics Technology, Aug. 1, 2001, 52.
Shin-Etsu Chemical Co., Ltd., "Silane Coupling Agents", Shin-Etsu Chemical Co., Ltd., Jun. 2017, 1-28.
Non-Final Office Action in U.S. Appl. No. 16/104,436, dated Mar. 2, 2020, 17 pages.
Non-Final Office Action in U.S. Appl. No. 16/104,442, dated Feb. 20, 2020, 19 pages.
Bailly, Mathieu , et al., "Preparation and characterization of thermoplastic olefin/nanosilica composites using a ilane-grafled polypropylene matrix", Polymer 50, Mar. 20, 2009, 2472-2480.
Viet, Dang Hoang, "Preparation of Antibacterial Polypropylene Grafted Acrylic Acid and Immobilized Silver Nanoparticles by Gamma-Irradiation Method", 2016, 699-704.

* cited by examiner

AMPHIPHILIC GRAFT COPOLYMERS AND MEDICAL DEVICES WITH ENHANCED BOND STRENGTH

CROSS-REFERENCE TO RELATED APPLICATIONS

This application claims priority under 35 U.S.C. § 119(e) to U.S. Provisional Application No. 62/547,167, filed Aug. 18, 2017, and U.S. Provisional Application No. 62/684,946, filed Jun. 14, 2018, the disclosures of which are incorporated herein by reference in their entireties.

TECHNICAL FIELD

Principles and embodiments of the present invention relate generally to amphiphilic graft copolymers and their applications for medical devices. Functionalized polypropylene copolymers disclosed herein are the copolymerization products of hybrid inorganic-organic micromolecules with polypropylene in the presence of a co-agent, for example, difunctional metallic diacrylate monomers. The polypropylene-based graft copolymers have a polypropylene backbone and hybrid micromolecule side-chains, which are based on organo-functional silanes and an inorganic portion (PP-g-XSiOA), where "X" is an organic group or an organo-functional group, and "A" is a metal, an inorganic oxide, an inorganic hydroxide, or any other inorganic material. Presence of PP-g-XSiOA in propylene-containing polyolefin or thermoplastic elastomer (TPE) formulations improves bonding between components of medical devices. For example, increases bonding strength between the tubing and connectors, where the connectors are made of different materials compared to the tubing.

BACKGROUND

Many components of medical devices are commonly made from polyolefin (e.g., ethylene- or propylene-containing) or thermoplastic elastomer (TPE) materials. Functional properties can be incorporated into known polymers to provide desired traits. U.S. Pat. No. 9,150,674 is directed to amphiphilic graft copolymers involving grafting either poly(ethylene oxide) or polylactide side chains onto known polymers, such as poly(ethylene-co-vinyl acetate) or maleic anhydride-grafted polypropylene.

Polypropylene (PP) and polypropylene based materials (PPBMs) such as thermoplastic olefins (TPO) or thermoplastic elastomer (TPE) compounds are popular materials among other plastics. Excellent chemical and heat resistance, ease of process, low scrap rates, and recyclability have earned PPBMs a market niche that continues to expand in the medical applications. PPBMs are considered viable candidates in medical tubing, drug storage, delivery devices, face masks, smart packaging and infant-care items applications where clarity, sterilization, and low extractables as well as bondability to a range of engineering thermoplastics and metal surfaces are highly desired. However, PPs and PPBMs are non-polar (absence of hydrophilic groups) and do not contain reactive functional groups that limits there applications in the fields where adhesion, solvent bondability, surface paintability, laser marking or dispersion of the polar additives (reinforcement, modifier or antimicrobial fillers) are highly desired.

There is a continuing need to develop polypropylene and PPBMs with high polarity in a cost-effective way.

SUMMARY

Provided are amphiphilic graft copolymers based on a polypropylene backbone and hybrid micromolecule side-chains based on organo-functional silanes and an inorganic portion in the presence of a co-agent, for example, difunctional metallic diacrylate monomers. They are functionalized polypropylene copolymers. The graft copolymers may be co-blended with base formulations to enhance properties of medical devices that are formed by injection molding or by extrusion.

In an aspect, an amphiphilic copolymer comprising polypropylene and an inorganic-organic hybrid micromolecule, the amphiphilic copolymer, is according to Formula (I):

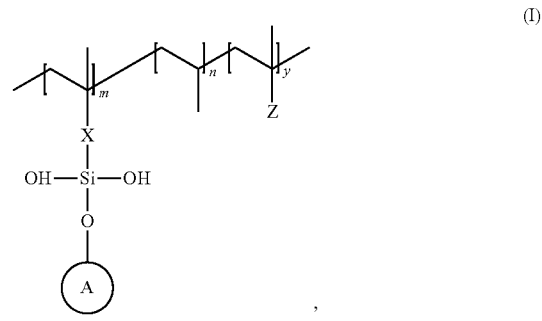

(I)

wherein X is an organic or an organo-functional group containing 1 to 6 carbons; A is a metal, an inorganic oxide, an inorganic hydroxide, or any other inorganic material; and n is in the range of about 78 to 99.9 mole percent; m is in the range of about 0.1 to 20 mole percent; the molar value of "y" is in the range of about 0 to 2.0 mole percent; and "Z", when y is greater than 0, comprises: $M-X_2$; XSiOR; or XSiOH, wherein "$M-X_2$" is an organo-metal salt and "OR" is an alkoxy group having 1 to 4 carbons.

The inorganic-organic hybrid micromolecule may be a reaction product of an organo-silane and an inorganic oxide and/or hydroxide.

X may be derived from a compound selected from the group consisting of: epoxy, amino, acrylate, methacryloxy, and vinyl; and A may be selected from the group consisting of: silicon, (Si), aluminum (Al), iron (Fe), titanium (Ti), silver (Ag), zinc (Zn), nickel (Ni), calcium (Ca), copper (Cu), tin (Sn); oxides thereof; hydroxides thereof; and mixtures of the foregoing.

The inorganic-organic hybrid micromolecule grafted to the polypropylene may be a reaction product of an organo-functional silane with an inorganic oxide and/or hydroxide in solution, wherein a weight ratio of the organo-functional silane to the inorganic oxide and/or hydroxide is at least 10:1.

In an embodiment, where y is 0, the amphiphilic copolymer is according to Formula (IA):

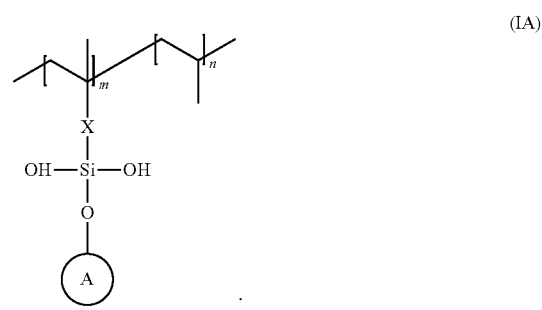

(IA)

In an embodiment, when X is derived from 3-(trimethoxysilyl)propyl methacrylate, the amphiphilic copolymer is according to Formula (VII):

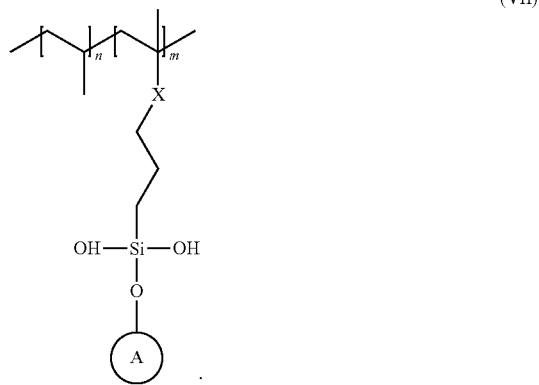

(VII)

In one or more embodiments, A may be derived from $Si(OH)_4$ or $SiO_2$.

The amphiphilic copolymer may have a melting point in the range of 140 to 180° C. The amphiphilic copolymer may have a capillary viscosity in the range of 100 to 300 Pa·s at 180 s$^{-1}$. The amphiphilic copolymer may have a weight average molecular weight (Mw) in the range of about 100,000 to about 350,000 g/mol. The amphiphilic copolymer may have a dispersity index in the range of 1.5 to 9. The amphiphilic copolymer may have a long chain branching frequency in the range of 0.007 to 0.017 per 1000 carbon. The amphiphilic copolymer may have a melt flow rate in the range of 15 to 55 g/10 minutes.

Another aspect is a process for preparing an amphiphilic copolymer comprising: obtaining polypropylene; polymerizing the polypropylene with an inorganic-organic hybrid micromolecule in the presence of a co-reagent that comprises a metal organic salt to form the amphiphilic copolymer; wherein the amphiphilic copolymer comprises a polypropylene backbone and side-chains based on one or more organo-functional silanes. The amphiphilic copolymer may be according to Formula (I).

The inorganic-organic hybrid micromolecule synthesis may be performed at a reaction temperature in the range of 20° C. to 35° C. The synthesis may be performed via solution polymerization.

Polymerization of the polypropylene with the inorganic-organic hybrid micromolecule in the presence of the co-reagent may be performed at a reaction temperature in the range of 150° C. to 250° C. The polymerization may be performed via melt polymerization or via solution polymerization. The co-agents may comprise an organo-metal salt based on difunctional diacrylate monomers.

A further aspect is a medical device formed from a blend comprising: a base polymeric formulation comprising at least a polymer or co-polymer of propylene; and an additive comprising a copolymer having a polypropylene backbone and hybrid micromolecule side-chains based on organo-functional silanes (PP-g-XSiOA), where "X" is an organic group or an organo-functional group; and "A" is a metal, an inorganic oxide, an inorganic hydroxide, or any other inorganic material; the PP-g-XSiOA being present in the blend in an amount in the range of about 0.01 to about 20.0% by weight of the blend. The PP-g-XSiOA may be according to Formula (I).

The base polymeric formulation may comprises polypropylene, a polyethylene-polypropylene co-polymer, a polypropylene-containing thermoplastic elastomer (TPE), or combinations thereof. The X of the PP-g-XSiOA may be derived from a compound selected from the group consisting of: epoxy, amino, acrylate, methacryloxy, and vinyl; and A may be selected from the group consisting of: silicon, (Si), aluminum (Al), iron (Fe), titanium (Ti), silver (Ag), zinc (Zn), nickel (Ni), calcium (Ca), copper (Cu), tin (Sn); oxides thereof; hydroxides thereof; and mixtures of the foregoing.

The PP-g-XSiOA may have a melting point in the range of 140 to 180° C. The PP-g-XSiOA may have a capillary viscosity in the range of 100 to 300 Pa·s at 180 s$^{-1}$. The PP-g-XSiOA may have a weight average molecular weight (Mw) in the range of about 100,000 to about 350,000 g/mol. The PP-g-XSiOA may have a dispersity index in the range of 1.5 to 9. The PP-g-XSiOA may have a long chain branching frequency in the range of 0.007 to 0.017 per 1000 carbon. The PP-g-XSiOA may have a melt flow rate in the range of 15 to 55 g/10 minutes. In one or more embodiments, the medical device has one or more improved characteristics relative to a comparative a base polymeric formulation without a PP-g-XSiOA additive selected from the group consisting of: laser printability and/or marking; solvent bonding, and melt adhesion to polar surfaces. The medical device may be in the form of tubing.

Another aspect is a medical device comprising: a tubing comprising a polymeric blend comprising a base polymeric formulation comprising at least a polymer or co-polymer of propylene and an additive comprising a copolymer having a polypropylene backbone and hybrid micromolecule side-chains based on organo-functional silanes (PP-g-XSiOA), where "X" is an organic group or an organo-functional group; and "A" is a metal, an inorganic oxide, an inorganic hydroxide, or any other inorganic material; wherein the PP-g-XSiOA is present in the blend in an amount in the range of about 0.01 to about 20.0% by weight of the blend; and a connector bonded to the tubing.

In one or more embodiments, the PP-g-XSiOA is effective to enhance bonding of the tubing to the connector. The PP-g-XSiOA may be according to Formula (I). The PP-g-XSiOA may be according to any embodiment disclosed herein.

The connector may comprise a metal. The metal may be selected from the group consisting of: steel, cobalt, titanium, tantalum, and their alloys. The metal connector may be melt-bonded to the tubing.

The connector may comprise a polar material. The polar material may be selected from the group consisting of: poly(methyl methacrylate) (PMMA), styrene maleic anhydride (SMA), polycarbonate (PC), and methyl methacrylate-acrylonitrile-butadiene-styrene (MABS). The polar material connector may be solvent-bonded to the tubing.

Another aspect is a method making a medical device comprising: obtaining a copolymer having a polypropylene backbone and hybrid micromolecule side-chains based on organo-functional silanes (PP-g-XSiOA), where "X" is an organic group or an organo-functional group; and "A" is a metal, an inorganic oxide, an inorganic hydroxide, or any other inorganic material; combining the PP-g-XSiOA with a base polymeric formulation comprising at least a polymer or co-polymer of propylene to form a blend, the PP-g-XSiOA being present in the blend in an amount in the range of about 0.01 to about 20.0% by weight of the blend; forming a tubing from the blend; and bonding the tubing to a connector in the absence of an adhesive to form the medical device. The PP-g-XSiOA may be according to Formula (I). The PP-g-XSiOA may be according to any embodiment disclosed herein. The connectors may be according to any embodiment herein.

DETAILED DESCRIPTION

Figure 1:
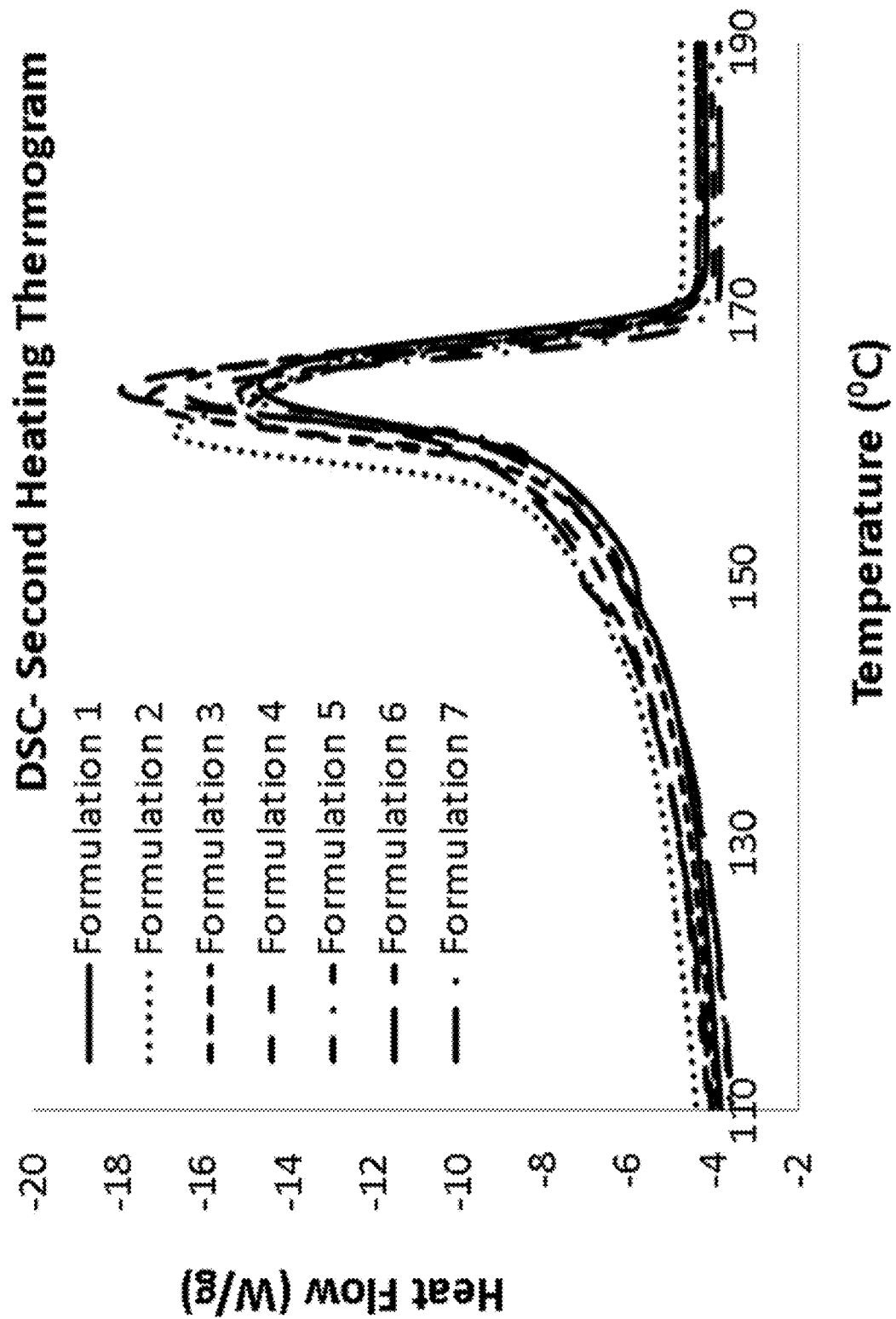
FIG. 1 is a thermogram of heat flow (W/g) for polymers according to formulations 1-7 versus temperature (° C.) for a first range of temperatures during a second heating.

Before describing several exemplary embodiments of the invention, it is to be understood that the invention is not limited to the details of construction or process steps set forth in the following description. The invention is capable of other embodiments and of being practiced or being carried out in various ways.

The present disclosure provides polypropylene (PP) and polypropylene based materials (PPBMs) with high polarity in a cost-effective way by way of a free radical modification process of PP via reactive modification using melt mixing reactor (hot melt extrusion).

Prior art has shown that neat silanes can be incorporated into polyethylene (PE) and that the functionalized derivatives can be moisture crosslinked/cured in water. Namely, the reactive groups of silane are grafted on the chains during a melt extruder process and later alcoholysis and dehydration of the grafted silane are induced by water to form Si—O—Si bonds between PE chains. This approach has capability to improve PE properties but such technology is complicated and costly because the processes require use of the catalyst and two-steps of process—grafting and crosslinking/curing afterwards.

In some polymer-based composite applications where compatibility between polymers and glass fibers is desired, organic-silane solutions (diluted solutions in alcohol) have been used as primers/coupling agents. That is, glass fibers have been coated in advance with silane primers and afterwards loaded in a polymer to provide functionality.

Advantageously, the present disclosure grafts hybrid micromolecule side-chains based on organo-functional silanes chemistry to a polypropylene backbone in the presence of a co-agent, for example, difunctional metallic diacrylate monomers to be used as a single component system or as an additive for thermoplastic elastomers to promote laser printing and/or marking as well as to promote melt and solvent bondability to the metal and polar polymer surfaces. The present disclosure does not involve polymer crosslinking or process preparing long chain branched polyolefins for a high melt strength applications or using organic-silane solutions as primers for the inorganic fillers; goal of this technology is to introduce amphiphilic groups into PP chain as well as to reinforce PP matrix by grafting hybrid micromolecules and to promote laser marking, antimicrobial resistance and adhesive free solvent bondability.

In one or more embodiments, modified (functionalized) polypropylene (PP) can be used as a single component or as an additive to improve solvent bondability and melt adhesion/compatibility of PP and PP-based thermoplastic elastomers (TPEs) with dissimilar plastic materials or metal substrates. Modified PPs are obtained by changing chemistry and subsequently hydrophilicity of PP and/or PP-based-TPE materials by incorporating functional groups based on hybrid organic silane micromolecules in combination with the difunctional metallic diacrylate monomers. Grafted functional groups in the modified PPs act as compatibilizer networks between dissimilar materials, which promotes solvent adhesion and melt interactions between interfaces of the dissimilar materials.

Modified PP and PPBMs can be beneficially used in making parts of the medical devices including, but not limited to balloon catheters; tubing for feeding, drainage, and use with peristaltic pumps; compression bars; electro-surgical hand pieces; infusion sleeves and test chambers; introducer tips and flexible sheaths; ear plugs and hearing aids; shunts and septums; and a variety of seals, stoppers, valves, and clips; as well as for applications such as IV tubing, catheter extension set tubing and catheter tubing. Modified PP and PPBMs may also be suitable for syringes for receipt of laser printing and/or marking. Moreover, modification technology has potential to improve unmet polyolefin based materials properties needs, such as: solvent bondability for tubing application; melt adhesion with metal and other polar materials surfaces for smart devices and packaging applications with integrated microchips, cameras or sensors; technology shows potential to improve additives dispersion and compatibility—to tailor materials properties (self-lubrication, stiffness)/or to enhance efficiency of the antimicrobial additives via homogeneous dispersion and improved interactions and to improve laser printing/writing on the medical devices surfaces made from PPBMs.

Principles and embodiments of the present invention relate to chemical modification of commodity polypropylene via a chemical grafting-approach to develop amphiphilic copolymers.

Synthesis of Functionalized-PP

The amphiphilic polypropylene-based graft copolymers of the present disclosure combine hybrid inorganic-organic micromolecules with polypropylene in the presence of a co-agent. The copolymers are in accordance with Formula (I):

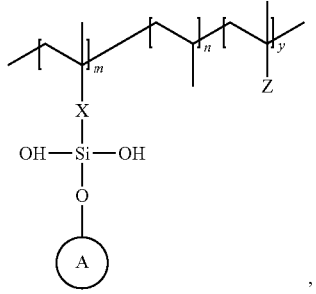

(I)

wherein "X" is an organic or an organo-functional group containing 1 to 6 carbons, "A" is a metal, an inorganic oxide, an inorganic hydroxide, or any other inorganic material, "n" is an integer that is in excess of 100, "m" is an integer that is 1 or greater, and "y" is 0 or a number greater than 0. X is derived from X', which is an organo-functional group containing 1 to 6 carbons, whose functionality includes a reactive group suitable for radical polymerization. The integer n is a very large number, and can represent hundreds or thousands of repeating units in one molecule. In one or more embodiments, n is an integer in the range of 100 to 1,000,000; or 500 to 750,000; or 1,000 to 500,000; and all values and subranges therebetween. Reference to "n" is with respect to propylene units, "m" is to grafted hybrid side chains, and "y" is to grafted secondary side chains ("Z"). The molar value of "m" is in the range of about 0.1 to 20 mole percent, the molar value of "y" is in the range of about 0 to 2.0 mole percent, and the molar value of "n" is in the range of about 78 to 99.9 mole percent. "Z", when y is greater than 0, comprises a secondary side chain: $M\text{-}X_2$; XSiOR; or XSiOH, wherein "$M\text{-}X_2$" is an organo-metal salt, "OR" is an alkoxy group having 1 to 4 carbons.

When "y" is 0, Formula (I) becomes Formula (IA):

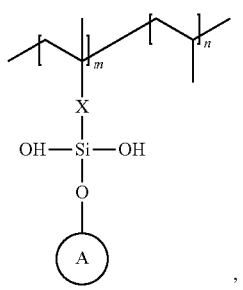

(IA)

In a first step, hybrid inorganic-organic micromolecules (AOSiX') are either synthesized in solution or commercially obtained. The hybrid micromolecules are effective to deliver desirable functionality to the copolymers when their grafting degree with respect to the polypropylene backbone is at least 0.1 mol. % of the amphiphilic copolymer (e.g., n is >=0.1 mol. %). The targeted hybrid micromolecules are according to general formula (II):

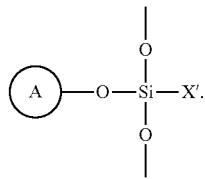

(II)

"X'" is an organo-functional group containing 1 to 6 carbons, whose functionality includes a reactive group suitable for radical polymerization. Reactive groups suitable for radical polymerization include, for example, ethylenically unsaturated groups, epoxies, acrylates and amines.

During synthesis of hybrid inorganic-organic micromolecules, secondary micromolecules may result from side reactions, $(OH)_3SiX'$, and incomplete hydrolysis reactions, $(OR)_3SiX'$.

Hybrid micromolecules may be generated by treating a precursor of "A". The precursors are inorganic materials including but not limited to inorganic oxides, inorganic hydroxides, and any inorganic materials with one or more hydroxyl groups on the surface, with "X'SiO", which is an organo-functional silane.

Inorganic materials, "A", which are the inorganic portion of the hybrid inorganic-organic micromolecules, may include but are not limited to one or more of the following: a metal, an inorganic oxide, an inorganic hydroxide, or any other inorganic material. In an embodiment, A is selected from the group consisting of: silicon, (Si), aluminum (Al), iron (Fe), titanium (Ti), silver (Ag), zinc (Zn), nickel (Ni), calcium (Ca), copper (Cu), tin (Sn); oxides thereof; hydroxides thereof; and mixtures of the foregoing. The precursor of "A" reacts by hydrolysis with one or more the organo-functional silanes having an ethylenically unsaturated group. A may be derived from, for example, $Si(OH)_4$ or $SiO_2$.

Organo-functional silanes, X'SiO, which are the organic portion of the hybrid inorganic-organic micromolecules, may be according to general formula (IV):

$$X'\text{—}Si(OR)_3 \qquad (IV),$$

wherein "OR" is an alkoxy group having 1 to 4 carbons, and "X'" is an organo-functional group, containing at least one reactive group suitable for radical polymerization. The organo-silanes thus contain two different types of reactive groups: the OR groups, which are easily hydrolysable groups such as methoxy or ethoxy groups suitable for hybrid inorganic-organic micromolecules (AOSiX') synthesis; and the X' group, which is an organo-functional group such as epoxy, amino, acrylate, methacryloxy, or vinyl suitable for radical polymerization. The inorganic-organic hybrid micromolecule is therefore a reaction product of an organo-silane and an inorganic oxide and/or hydroxide.

Si—OR bonds hydrolyze readily with water (even if only moisture adsorbed on the surface) to form Si—OH groups. Si—OR bonds can also be readily condense with hydroxyl groups on the surface of inorganic oxides, hydroxides, minerals or metals to form stable Si—O-A bonds (A=Si, Al, Fe, and the like) thus hybrid micromolecules are formed through hydrolysis, condensation process that takes place between organo-functional silane micromolecules and the hydroxide groups of the inorganic materials (fillers).

Hybrid materials may be synthesized at room temperature by dispersing the precursor of "A", e.g., inorganic oxide or hydroxide powder, in an organo-functional silane solution, wherein a weight ratio of the organo-functional silane group to precursor is at least 10:1. That is, in one or more embodiments, the amount of the organo-functional silane group to precursor is at least 10 times that of precursor to achieve completion of hybrid materials synthesis. In one or more embodiments, the weight ratio of organo-functional silane to the inorganic oxide or hydroxide precursor to is in the range of 10:1 to 1000:1. The dispersion is then ultrasonicated for at least 3 hours to form targeted hybrid micromolecules are according to general formula (II).

Figure 9:
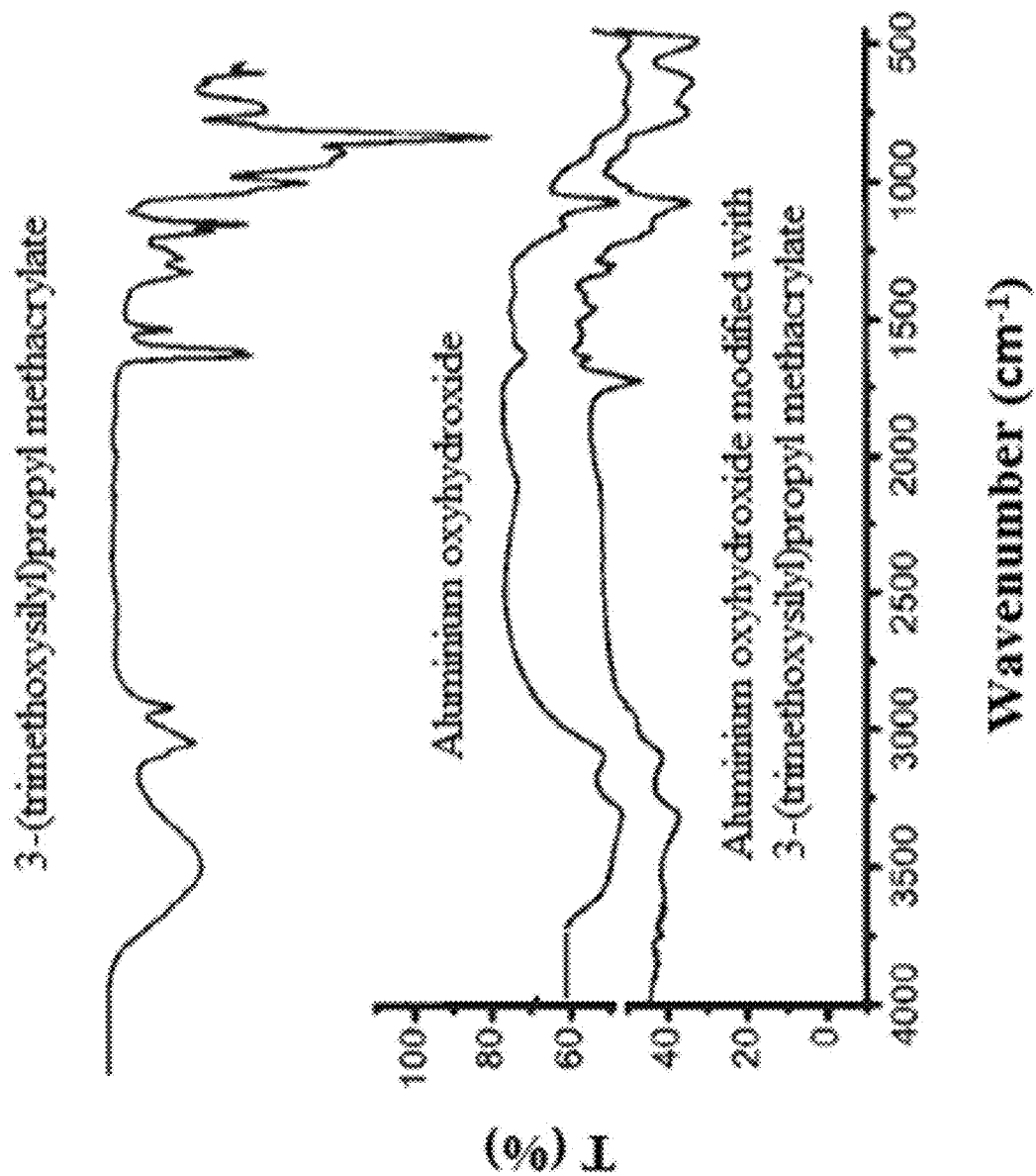
FIG. 9 provides FTIR spectra of exemplary hybrid inorganic-organic micromolecules based on aluminum oxyhydroxide and 3-(trimethoxysilyl)propyl methacrylate.

An exemplary hybrid material may be formed using a silicon dioxide ($SiO_2$) and 3-(trimethoxysilyl)propyl methacrylate according to equation (a-1):

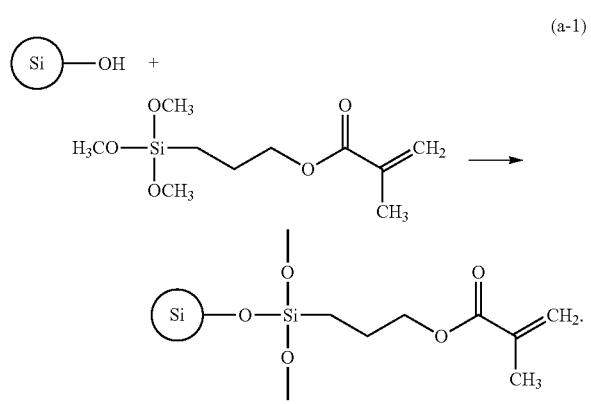

wherein 3-(trimethoxysilyl)propyl methacrylate is a precursor with tri methoxy groups. Degree of functionality of hybrid material may be monitored by FTIR and 1H-NMR; for example for 3-(trimethoxysilyl)propyl methacrylate based hybrid micromolecules functionality is measured by monitoring formation of characteristic carbonyl (C=O) stretching vibration at 1500-1750 $cm^{-1}$ FTIR range (see FIG. 9).

Silicones (polysiloxanes) are an exemplary group of inorganic-organic hybrid compounds, composed of silicon and oxygen atoms in the main chains and organic substituents bound to silicon. Silicones are mainly applied as silicone oils, rubbers, and they are also used to modify polymer properties. In addition to silicones, reactive silanes, siloxanes, and silicates, are also used for the modification of polymer properties. Silane used in this invention is commercially available from the Mitsubishi Corporation, Evonik and the Struktol.

Functional organosilanes suitable for use in this process include, but are not limited to, tetraethoxysilane, methyltrimethoxysilane, methyltriethoxysilane, dimethyldimethoxysilane, propyltrimethoxysilane, propyltriethoxysilane, iso-butyltrimethoxysilane, iso-butyltriethoxysilane, phenyltrimethoxysilane, n-octyltriethoxysilane, methacryloxypropyltrimethoxysilane, chloropropyltriethoxysilane, methyldimethoxysilane, phenyltriethoxysilane, chloropropyltrimethoxysilane, aminoethylaminopropyltrimethoxysilane, glycidoxypropyltrimethoxysilane, vinyltriethoxysilane, tetraethoxysilane, (3-acetamidopropyl)trimethoxysilane, acetoxyethyldimethylchlorosilane, acetoxyethylmethyldichlorosilane, acetoxyethyltrichlorosilane, acetoxyethyltriethoxysilane, acetoxyethyltrimethoxysilane, acetoxyethyltris(dimethylamino)silane, acryloxymethyltrimethysilane, allyltrichlorosilane, allyltriethoxysilane, allyltri-iso-propylsilane, allyldimethylchlorosilane, allylmethyldichlorosilane, allylmethyldimethoxysilane, allyltrimethoxysilane, allylphenyldichlorosilane, 3-acrylamidopropyltris(trimethylsiloxy)silane.

During polymerization, a free-radical initiator is present. Peroxide-based free-radical initiators are preferred, specifically organic peroxides. Exemplary organic peroxides include but are not limited to, cyclic peroxides, diacyl peroxides, dialkyl peroxides, hydroperoxides, peroxycarbonates, peroxydicarbonates, peroxyesters, peroxyketals, and mixtures thereof.

Exemplary peroxides include: dihexylene glycol peroxide; 4-(t-hexylperoxy)-4-methyl-2-pentanol; 4-(t-octylperoxy)-4-methyl-2-pentanol; 2-methyl-2-t-amylperoxy-4-pentanone; di-t-hexyl peroxide; di-t-octyl peroxide; the t-amyl, t-hexyl and t-octyl analogs of LUPEROX 101; analogs of Perkadox 24L (dicetyl peroxydicarbonate) and Perkadox 16; mixed dialkyl peroxides such as t-amyl-t-hexyl peroxide and t-amyl-t-octyl peroxide.

An exemplary free-radical initiator is 2,5-bis(tert-butylperoxy)-2,5-dimethylhexane, which is sold under the tradename LUPEROX 101, according to formula (V):

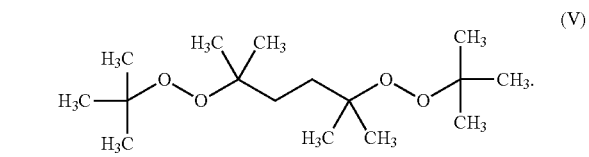 [SMILES: CC(C)(C)OOC(C)(C)CCC(C)(C)OOC(C)(C)C]

The grafting reaction of hybrid side chains onto a polypropylene (PP) backbone proceeds according to equations (b) to (c). As a starting polymer, commercially available polypropylene homopolymers can be used with melt values in the range of 0.5-20 g/10 minutes.

In a first step according to equation (b), there is free radical formation by thermal decomposition of organic peroxide and formation of the macro radical.

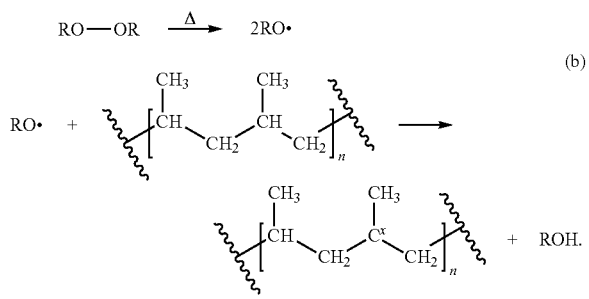

In a second step according to (c), there is grafting of hybrid micromolecules according to general formula (II) onto the polypropylene chain.

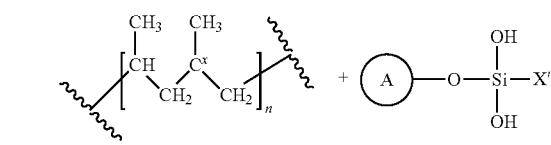

wherein A is a metal, an inorganic oxide, an inorganic hydroxide, or any other inorganic material and X' is a group selected from: epoxy, amino, acrylate, methacryloxy, and vinyl.

For the specific hybrid micromolecules obtained by equation (a-1), and accounting for possible secondary reactions during hybrid synthesis (X'SiOR and X'SiOH), the amphiphilic copolymer is according to (VI).

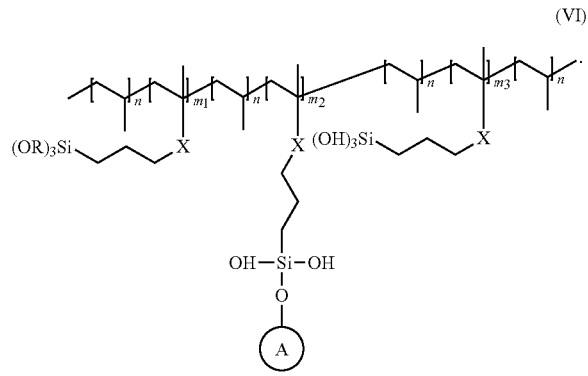

(VI)

wherein the molar value of "$m_1+m_2+m_3$" is in the range from 0.1 to 20 mole percent; and the molar value of "n" is in the range from 80 to 99.9 mole percent. When $m_1$ and $m_3$ are 0 or the secondary chains are negligible, the amphiphilic copolymer when using the hybrid of (a-1) has a structure according to (VII):

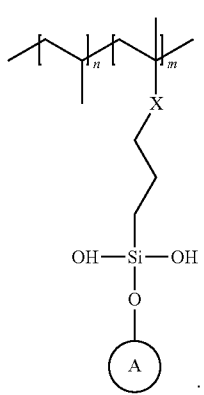

(VII)

wherein X is methacrylate, "m" is in the range of 0.1 to 20 mole percent, "n" is in the range from 80 to 99.9 mole percent.

Hybrid inorganic-organic micromolecules are copolymerized with polypropylene in the presence of a co-agent, for example, difunctional metallic diacrylate monomers. A co-agent is present during polymerization to stabilize radicals and reduce chain scission of the polypropylene backbone. Free radical processes start with formation of macroradicals along the polymer chains by a so-called hydrogen abstraction mechanism as shown in equation (a). The macroradicals might subsequently follow two competing pathways. They could either initiate the grafting of the monomer or undergo chain scission. The latter depends strongly on the nature of the polymer backbone. In case of PP, the main side reaction is β-scission associated with PP macroradicals, which cause a reduction in the molecular weight of the polymer. In the prior art, styrene was found to be a good comonomer to promote radical grafting and to reduce chain scission of a PP matrix. It was believed to relate to the reactivity towards PP macroradicals; namely, to obtain high grafting yields and to reduce side reactions, it was preferred that the macroradicals react with the grafting monomer rather than undergo side reactions. The so-called 'styrene comonomer concept' was developed in the prior art to improve the grafting yields during free radical modification of polyolefins with maleic anhydride, glycidyl methacrylate and vinyl and acrylic monomers. Cartier H., Hu G-H.: Styrene-assisted melt free radical grafting of glycidyl methacrylate onto polypropylene. Journal of Polymer Science, Part A: Polymer Chemistry, 36, 1053-1063 (1997); Hu G-H., Cartier H.: Styrene-assisted melt free radical grafting of glycidyl methacrylate onto an ethylene and propylene rubber. Journal of Applied Polymer Science, 71, 125-133 (1999); and Cartier H., Hu G-H.: Styrene-assisted free radical grafting of glycidyl methacrylate onto polyethylene in the melt. Journal of Polymer Science Part A: Polymer Chemistry, 36, 2763-2774 (1998). Styrene monomers not advantageous for the purposes of preparing medical devices in that they are considered to provide moderate toxicity and high flammability. In this invention, metal salts having organic functional groups have been selected instead as radical stabilizers. Specifically, diacrylate and/or dimethacryolate monomers offer high temperature stability, easy and safe processability; they are available commercially and used as curing agents for epoxy, rubber, and adhesive systems.

Exemplary co-agents are organo-metal salts. The organo-metal salts may be according to general formula (VI):

$$M-X_2 \quad (VI),$$

wherein "M" is a metal selected from the group consisting of Na, Ca, Mg, Zn, Al and Fe (III). "$X_2$" is an organo-functional group containing at least one double bond, independent from the organo-functional silanes ("X'"). In a preferred embodiment "$X_2$" of the co-reagent is the same as "X" of the organo-functional silane. In a preferred embodiment "$X_2$" is (meth)acrylate, which is defined to include both methacrylates and acrylates.

Exemplary co-agents include but are not limited to difunctional zinc diacrylate or zinc dimethacrylate co-agent according to formulas VIII-A and VIII-B, respectively.

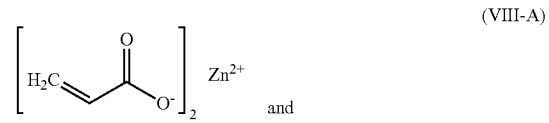

(VIII-A)

and

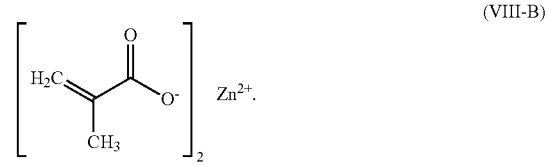

(VIII-B)

The radical stabilization reaction proceeds according to (d) when, for example, a zinc (meth)acrylate is used.

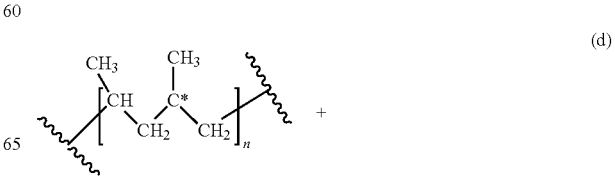

(d)

-continued

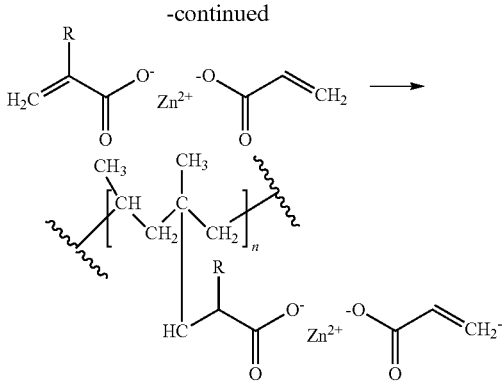

wherein R is H or CH$_3$.

It is understood that there is the potential for grafting on to PP difunctional metallic diacrylate side-chains, according to equation (d-1):

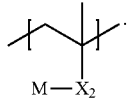

(d-1)

Difunctional zinc diacrylate and zinc dimethacrylate monomers are commercially available product from Sartomer, Westman Chemicals, Crayvalley, Shokubai and Esstech, Inc. Acrylic and methacrylic salts suitable for use in this process include salts of Na, Ca, Mg, Zn, Al and Fe (III).

In one or more embodiments, the amphiphilic graft copolymer has a melting point in the range of 140 to 180° C.

In one or more embodiments, the amphiphilic graft copolymer has a capillary viscosity in the range of 100 to 300 Pa·s at 180 s$^{-1}$.

In one or more embodiments, the amphiphilic graft copolymer has a weight average molecular weight (Mw) in the range of about 100,000 to about 350,000 g/mol.

In one or more embodiments, the amphiphilic graft copolymer has a dispersity index in the range of 1.5 to 9, or 1.5 to 8, or 1.5-5.

In one or more embodiments, the amphiphilic graft copolymer has a long chain branching frequency in the range of 0.007 to 0.017 per 1000 carbon.

In one or more embodiments, the amphiphilic graft copolymer has a melt flow rate in the range of 15 to 55, or 20 to 40, or 25-35 g/10 minutes in accordance with ASTM 1238-13 method.

In one or more embodiments, polymerization is performed at a reaction temperature in the range of 20° C. to 40° C. In a specific embodiment, the polymerization is performed at a reaction temperature of about 25° C.

In one or more embodiments, the polymerization is performed by solution polymerization. In one or more embodiments, the polymerization is performed by melt processing.

Polymerization

Solution polymerization may be used for the synthesis, where the starting materials are in a solvent-based solution. Melt processing may also be used, which may include a twin screw extruder above melting temperature of PP. The term "melt processing" is used to mean any process in which polymers, such as the polyolefin, are melted or softened. Melt processing includes extrusion, pelletization, film blowing or casting, thermoforming, compounding in polymer melt form, fiber spinning, or other melt processes.

Any equipment suitable for a melt processing can be used as long as it provides sufficient mixing and temperature control. For instance, a continuous polymer processing system such as an extruder, a static polymer mixing device such as a Brabender blender, or a semi-continuous polymer processing system, such as a BANBURY mixer, can be used. The term "extruder" includes any machine for polyolefin and TPE extrusion. For instance, the term includes machines that can extrude material in the form of powder or pellets, sheets, fibers, or other desired shapes and/or profiles. Generally, an extruder operates by feeding material through the feed throat (an opening near the rear of the barrel) which comes into contact with one or more screws. The rotating screw(s) forces the polyolefin forward into one or more heated barrels (e.g., there may be one screw per barrel). In many processes, a heating profile can be set for the barrel in which three or more independent proportional-integral-derivative controller (PID)-controlled heater zones can gradually increase the temperature of the barrel from the rear (where the plastic enters) to the front. When a melt extrusion is used, the mixing can take place during the melt extrusion step. The heat produced during the extrusion step provides the energy necessary for the mixing between different components. A temperature at or above the melting temperature of the polymer may be maintained for a time sufficient to mix all the components. For instance, the mixing time may be at least 5 seconds, at least 10 seconds, or at least 15 seconds. Typically, the mixing time is 15-90 seconds.

Blends for Medical Devices

A base polymeric formulation is a material from which a medical device may be made. Preferably, the base polymeric formulations utilized in conjunction with the amphiphilic graft copolymers disclosed herein comprise at least a polymer or co-polymer of ethylene or polyethylene. The base formulation may further include other ingredients, independently selected from one or more of the following: reinforcing and non-reinforcing fillers, plasticizers, antioxidants, stabilizers, processing oil, extender oils, lubricants, anti-blocking, antistatic agents, waxes, foaming agents, pigments, flame retardants and other processing aids known in the compounding art. Fillers and extenders which can be utilized include conventional inorganics such as calcium carbonate, clays, silica, talc, titanium dioxide, carbon black, and the like. The processing oils generally are paraffinic, naphthenic or aromatic oils derived from petroleum fractions. The oils are selected from those ordinarily used in conjunction with the specific plastics or rubbers present in the formulation.

An additive is a component added to a formulation which is not reactive within the formulation.

Base polymeric materials with PP-g-XSiOA additive prepared with according to the process of the invention may be formed into useful articles by standard forming methods known in the art, e.g., by blown film extrusion, cast film extrusion, injection or blow molding, pelletizing, foaming, thermoforming, compounding in polymer melt form, or fiber spinning. For example, any technique discussed above in the embodiments describing the melt processes can be used to prepare modified polymer, thereby forming various useful articles, depending on the type of melt processing technique used. For instance, blend may be used in making films, such as blown or cast films. The techniques of blown film extrusion and cast film are known to one skilled in the art in the area of production of thin plastic films. Polymers with PP-g-XSiOA additive may also be used in coextruded films.

The formation of coextruded blown films is known to one skilled in the art. The term "coextrusion" refers to the process of extruding two or more materials through a single die with two or more orifices arranged such that the extrudates merged together into a laminar structure, for instance, before chilling or quenching.

TABLE I

Exemplary Formulations (with the proviso that the ingredients total 100%).

| Blend Ingredient | A by weight | B by weight | C by weight |
| --- | --- | --- | --- |
| Base Polymeric Formulation | 80-99.99% | 80-99.99% | 80-99.99% |
| Polypropylene | 50-100% | 0-50% | 0-50% |
| Polyethylene | 0-50% | 50-100% | 0-50% |
| Polypropylene-containing Thermoplastic elastomer (TPE) | 0-50% | 0-50% | 50-100% |
| Optional further ingredients | 0-10% | 0-10% | 0-10% |
| PP-g-XSiOA additive | 0.01-20% | 0.01-20% | 0.01-20% |

In one or more embodiments, including Exemplary Formulations A, B, and C, the PP-g-XSiOA additive may be present in amounts of about 0.01 to about 10.0% by weight; about 0.1 to about 5.0% by weight; about 0.2 to about 2.0% by weight; about 0.25 to about 0.75% by weight; or about 0.5 weight %.

Polypropylene may be any commercially-available material produced by Ziegler-Natta, Metallocene, or any other olefin polymerization catalyst. Propylene polymers may be homopolymers or copolymers (random or impact). In applications where polypropylene (PP) and polyethylene blends are used, random and impact PP copolymers are preferred; improved compatibility of propylene and ethylene polymers comes from C2 content in the random PP grades. Higher compatibility results in improved physical and mechanical properties for the resulting articles (such as improved tear, dart impact, or puncture resistance in films) as compared with the homopolymer PP resin. The propylene polymers are preferably isotactic or syndiotactic, more preferably isotactic. The preferably melt flow rate of the propylene polymers is in the 0.5-150 g/10 minutes range based on the requirements of the manufacturing process and end applications (230° C./2.16 kg, ASTM D1238-13).

Suitable linear low density polyethylene (LLDPE) for use in the process of the invention include copolymers of ethylene and α-olefins. Alpha-olefins include 1-butene, 1-hexene, and 1-octene, the like, and mixtures thereof. The density of LLDPE is preferably within the range of about 0.865 to about 0.925 g/cm$^3$ (ASTM D792-13) and a melt mass flow rate of less than 0.5 g/10 min to greater than 20 g/10 min based on the requirements of the manufacturing process and end application (190° C./2.16 kg, ASTM D1238-13). LLDPE is commercially available, for instance Dowlex™ 2045.01 G LLDPE from Dow Chemical Company. Suitable LLDPE can be produced by a Ziegler-Natta, single-site, or any other olefin polymerization catalysts.

Suitable polyethylene-polypropylene co-polymers may include—reactor grade or melt blended mixtures of the polypropylene and polyethylene polyolefins with or without polyolefin elastomers (final formulation containing from but not limited to about 10 wt.-% up to about 80 wt.-% ethylene and/or propylene monomeric units). The term "blend" or "polymer blend" generally refers to a mixture of two or more components. Such a blend may or may not be miscible, and may or may not be phase separated.

Suitable polyolefins include those prepared from linear or branched olefins having 2 to 20 carbon atoms, 2 to 16 carbon atoms, or 2 to 12 carbon atoms. Typically, the olefin used to prepare the polyolefin is α-olefin. Exemplary linear or branched α-olefins includes, but are not limited to, ethylene, propylene, 1-butene, 2-butene, 1-pentene, 3-methyl-1-butene, 4-methyl-1-pentene, 3-methyl-1-pentene, 1-hexene, 3,5,5-trimethyl-1-hexene, 4,6-dimethyl-1-heptene, 1-octene, 1-decene, 1-undecene, 1-dodecene, 1-tetradecene, 1-hexadecene, 1-octadecene, and 1-eicosene. These olefins may contain one or more heteroatoms such as an oxygen, nitrogen, or silicon. The term "polyolefin" generally embraces a homopolymer prepared from a single type of olefin monomer as well as a copolymer prepared from two or more olefin monomers. A specific polyolefin referred to herein shall mean polymers comprising greater than 50% by weight of units derived from that specific olefin monomer, including homopolymers of that specific olefin or copolymers containing units derived from that specific olefin monomer and one or more other types of olefin comonomers. The polyolefin used herein can be a copolymer wherein the comonomer(s) is/are randomly distributed along the polymer chain, a periodic copolymer, an alternating copolymer, or a block copolymer comprising two or more homopolymer blocks linked by covalent bonds. Typical polyolefins include polyethylene, polypropylene, a copolymer of polyethylene and polypropylene, and a polymer blend containing polyethylene, polypropylene, and/or a copolymer of polyethylene and polypropylene. Polyolefin can also be an ethylene rich impact copolymer (may contain ethylene comonomer at the amount of at least 10 wt.-%; and up to 40 wt.-%), i.e., a heterophasic polyolefin copolymer where one polyolefin is the continuous phase and an elastomeric phase is uniformly dispersed therein. This would include, for instance, a heterophasic polypropylene copolymer where polypropylene is the continuous phase and an elastomeric phase is uniformly dispersed therein. The impact copolymer results from an in-reactor process rather than physical blending. The polyolefins mentioned above can be made by conventional Ziegler/Natta catalyst-systems or by single-site catalyst-systems.

Suitable polyolefin elastomers for use in the process of the invention include ethylene-propylene rubber (EPR), ethylene-propylene-diene monomer rubber (EPDM), the like, and mixtures thereof. As used herein, the term "elastomer" refers to products having rubber-like properties and little or no crystallinity. Preferably, the polyolefin elastomers contain from about 10 wt.-% up to about 80 wt.-% ethylene monomeric units. Illustrative polyolefin elastomers which are commercially available include Lanxess Corporation's BUNA EP T 2070 (22 Mooney ML(1+4) 125° C., 68% ethylene, and 32% propylene); BUNA EP T 2370 (16 Mooney, 3% ethylidene norbornene, 72% ethylene, and 25% propylene); BUNA EP T 2460 (21 Mooney, 4% ethylidene norbornene, 62% ethylene, and 34% propylene); ExxonMobil Chemical's VISTALON 707 (72% ethylene, 28% propylene, and 22.5 Mooney); VISTALON 722 (72% ethylene, 28% propylene, and 16 Mooney); and VISTALON 828 (60% ethylene, 40% propylene, and 51 Mooney). Suitable EP elastomers available from commercial sources also include ExxonMobil Chemical's VISTAMAXX series of elastomers, particularly VISTAMAXX grades 6100, 1100, and 3000. These materials are ethylene-propylene elastomers of 16, 15, and 11 wt.-% ethylene content, respectively, and a Tg of about −20 to −30° C. VISTAMAXX 6100, 1100, and 3000, respectively, have a melt flow rate of 3, 4, and 7 g/10 minutes at 230° C.; a density of 0.858, 0.862, and 0.871 g/cm$^3$; and a 200 g Vicat softening point of 48, 47, and 64° C. Other suitable elastomers include Dow Chemical's VERSIFY propylene-ethylene copolymers, particularly grades DP3200.01, DP3300.01, and DP3400.01, which have nominal ethylene contents of 9, 12 and 15 wt.-%, respectively, and corresponding nominal propylene contents of 91, 88, and 85 wt.-%, respectively. These grades have a melt flow rate of 8 g/10 minutes at 230° C.; a density of 0.876, 0.866, and 0.858 g/cm$^3$, respectively; a Vicat softening point of 60, 29, and <20° C., respectively; and a Tg of −25, −28, and −31° C., respectively.

Preferably, the polyolefin elastomers contain from but not limited to about 10 wt.-% up to about 80 wt.-% ethylene monomeric units. The term "thermoplastic elastomer" (TPE) in general defines blends of polyolefins and rubbers in which blends of the rubber phase is not cured, i.e., so called thermoplastic olefins (TPO), blends of polyolefins and rubbers in which blends of the rubber phase has been partially or fully cured by a vulcanization process to form thermoplastic vulcanizates (TPV), or unvulcanized block-copolymers or blends thereof. Non-polar thermoplastic elastomer may made from a thermoplastic polyolefin homopolymer or copolymer, and an olefinic rubber which is fully crosslinked, partially crosslinked or not crosslinked, and optionally commonly used additives; as well as a block-copolymer of styrene/conjugated diene/styrene and/or its fully or partially hydrogenated derivative.

Polyolefins suitable for use in TPE composition include thermoplastic, crystalline polyolefin homopolymers and copolymers. They are desirably prepared from monoolefin monomers having but not limited to 2 to 7 carbon atoms, such as ethylene, propylene, 1-butene, isobutylene, 1-pentene, 1-hexene, 1-octene, 3-methyl-1-pentene, 4-methyl-1-pentene, 5-methyl-1-hexene, mixtures thereof and copolymers thereof with (meth)acrylates and/or vinyl acetates. The polyolefins which can be used in TPE formulations can be a high, low, linear-low, very low-density polyethylenes and copolymers of ethylene with (meth)acrylates and/or vinyl acetates. Polyolefins can be made by conventional Ziegler/Natta catalyst-systems or by single-site catalyst-systems, or other polyolefin catalyst technology in combination with various process technologies and solutions.

Suitable olefinic rubbers of the monoolefin copolymer rubbers comprise non-polar, rubbery copolymers of two or more a-monoolefins, preferably copolymerized with at least one polyene, usually a diene. Saturated monoolefin copolymer rubber, for example ethylene-propylene copolymer rubber (EPM) can be used. However, unsaturated monoolefin rubber such as EPDM rubber is more suitable. EPDM is a terpolymer of ethylene, propylene and a non-conjugated diene. Satisfactory non-conjugated dienes include 5-ethylidene-2-norbornene (ENB); 1,4-hexadiene; 5-methylene-2-norbornene (MNB); 1,6-octadiene; 5-methyl-1,4-hexadiene; 3,7-dimethyl-1,6-octadiene; 1,3-cyclopentadiene; 1,4-cyclohexadiene; dicyclopentadiene (DCPD) and vinyl norbornene (VNB). Butyl rubbers are also used in TPE formulation. The term "butyl rubber" includes copolymers of an isoolefin and a conjugated monoolefin, terpolymers of an isoolefin with or without a conjugated monoolefin, divinyl aromatic monomers and the halogenated derivatives of such copolymers and terpolymers. Another suitable copolymer within the olefinic rubber is a copolymer of a $C_{4-7}$ isomonoolefin, and a para-alkylstyrene. A further olefinic rubber used in TPE is natural rubber. The main constituent of natural rubber is the linear polymer cis-1,4-polyisoprene. Furthermore polybutadiene rubber and styrene-butadiene-copolymer rubbers can also be used. Blends of any of the above olefinic rubbers can be employed, rather than a single olefinic rubber. Further suitable rubbers are nitrite rubbers. Examples of the nitrile group-containing rubber include a copolymer rubber comprising an ethylenically unsaturated nitrile compound and a conjugated diene. Further, the copolymer rubber may be one in which the conjugated diene units of the copolymer rubber are hydrogenated. Specific examples of the ethylenically unsaturated nitrile compound include acrylonitrile, α-chloroacrylonitrile, α-fluoroacrylonitrile and methacrylonitrile. Among them, acrylonitrile is particularly preferable. Other suitable rubbers are based on polychlorinated butadienes such as polychloroprene rubber. These rubbers are commercially available under the trade names Neoprene® and Bayprene®.

A commercially available thermoplastic elastomer (TPE) for use herein may be one formulated without plasticizers having a nominal density of 0.888 g/cm$^3$ (ASTM D792-13) and a nominal composition of: 33.0 mol % propylene, 24.8 mol % ethylene, and 42.2 mol % butylene.

Applications

The amphiphilic graft copolymers in the form of functionalized-PP materials may advantageously be used as modifier in a base polymer formulation, e.g., TPE or polyolefins. The modified base polymer formulations have improved properties with respect to, for example, blending, bonding, paintability, dyeability, laser printability and/or marking. The amphiphilic graft copolymers may be co-blended with base formulations to enhance properties of medical devices that are formed by injection molding or by extrusion.

The amphiphilic graft copolymers may be blended with polyolefins or TPE for forming medical devices. Suitable blending temperature during melt mixing should be sufficient to melt or to soften the component of the composition which has the highest melting or softening point. The temperature typically ranges from 60 to 300° C., for instance, from 100 to 280° C., from 90 to 150° C. One skilled in the art understands that a polyolefin or TPE mixtures thereof typically melts or softs over a temperature range rather than sharply at one temperature. Thus, it may be sufficient that the polyolefin be in a partially molten state. The melting or softening temperature ranges can be approximated from the differential scanning calorimeter (DSC) curve of the polyolefin or mixtures thereof.

Modified PP and PPBMs can be beneficially used (as a single component and as an additive) in making parts of the medical devices including, but not limited to balloon catheters, tubing for feeding, drainage, and use with peristaltic pumps, compression bars, electrosurgical hand pieces, infusion sleeves and test chambers, introducer tips and flexible sheaths, ear plugs and hearing aids, shunts and septums and a variety of seals, stoppers, valves, and clips; as well as for applications such as IV tubing, catheter extension set tubing and catheter tubing. For all of these applications there is a drive further enhance, and differentiate, the performance attributes of these devices and components. There is an additional desire from GPOs, NGOs, and regulatory to remove DEHP and other phthalate-based plasticizers from the formulation as well as to eliminate the use of PVC entirely.

Many TPE formulations use some type of plasticizer in their formulation and most IV tubing and extension sets are comprised of plasticized PVC. Additionally, for the stopper application there is a desire to move from the conventional thermal-set rubbers to an injection moldable thermoplastic elastomer which can also be reprocessed, resulting in processing efficiencies and potential cost savings.

For IV tubing TPE formulations cannot yet meet the desired performance attributes of plasticized PVC. Plasticized PVC is desired for its low set, high kink resistance, deformation recoverability, clarity, and tactile feel. An additional challenge with non-polar TPEs is the bonding of the IV tubing to connectors and other fixtures. These connections are typically done via solvent bonding.

For catheter tubing, some materials lose up to 20% of its strength in regions of elevated temperature and humidity, and causes difficulty in catheter stick, threading, advancing, and other catheter related complications.

The present disclosure can be used to address these problems.

Moreover, modification technology has potential to improve unmet PP based materials properties needs, such as—laser writing/printing (for marking medical devices), solvent bondability for tubing application; melt adhesion with metal and other polar materials surfaces for smart devices, and packaging applications with integrated microchips, cameras or sensors; shows potential to improve additives dispersion and compatibility—to tailor materials properties (self-lubrication, stiffness)/or to enhance efficiency of the antimicrobial additives via homogeneous dispersion and improved interactions.

Adhesive-Free Bonding

Reliability and reproducibility are desirable for manufacturing of medical devices. Non-compatible materials, for example: plastic/metal, metal/metal, mix-matched polymers, used in the manufacture of medical devices pose difficulties during assembly of the devices. A concern when bonding materials is how to get a strong bond between substrates of dissimilar materials. Generally, when bonding like materials, there are adhesives, solvents, or other types of techniques that will strongly bond two surfaces at the interface of the substrates. However, in many manufacturing scenarios, the need to bond different materials with very dissimilar physical and chemical properties can arise. For example, a reasonably rigid material such as polycarbonate (PC) may need to be bonded to a more elastic polypropylene (PP), polyethylene (PE), or thermoplastic elastomer (TPE) material. Since the chemical composition of these materials is quite different, they will tend to bond differently to various adhesives. A certain adhesive may bond well to the PC, but not well—if at all—to the PP, PE, TPE and vice versa. There are methods to chemically treat the surface of one or both of the materials using primers, or other mechanical means, such as changing roughness, to get a strong adhesive bond. While many of these methods may be adequate, they require use of materials that may contain toxic or materials of concerns (MOC) containing products. Such materials may also require expensive or time-consuming disposal methods. Most importantly, many toxic or MOC materials cannot be used in the manufacture of medical devices. Another, commonly-used technique for joining molded plastic parts of medical devices is solvent bondability. During a bonding process, the solvent dissolves the surface of the two mating parts and allows the material to flow together. Once the solvent evaporates, the result is a material-to-material bond. Many parts of medical devices made from plastics can be solvent-bonded in an application where ultrasonic bonding or adhesives do not work. However, for dissimilar materials, solvent may not achieve a satisfactory bonding. Namely, due to the hydrophobicity and low surface energy, polyolefins (PP, PE and its co-polymers) and thermoplastic elastomers (TPEs) demonstrate poor interaction and solvent bonding with dissimilar materials such as poly(methyl methacrylate) (PMMA), styrene maleic anhydride (SMA), polycarbonate (PC), and methyl methacrylate-acrylonitrile-butadiene-styrene (MABS) which are typically used for making parts of medical devices (for example connectors). Moreover, there are limited numbers of the applicable solvents, which are not flammable, not carcinogenic, and do not cause mechanical stress of the parts. There is thus a need to develop materials/technology solutions accordingly. Herein disclosed is a technology that allows the incorporation of polar functional groups that can be used to make strong bonding and improve compatibility between mismatched materials in a cost-effective way using melt- and/or solvent-bonding approaches. The modified PP compounds disclosed herein improve and enable solvent bondability and melt adhesion/miscibility between two dissimilar materials.

One targeted application is TPE tubing for medical devices. Plasticized polyvinyl chloride (PVC) is widely used for medical tubing applications, however, PVC is considered to be undesirable material not only because of the migration of the plasticizer to the surface but also because halogen-containing compounds are not favored. There is interest to develop an alternative non-halogen material for the medical tubing application to replace the plasticized PVC. TPE and other polyolefin materials have been identified as promising alternative candidates for PVC medical tubing, however non-polar nature of polyolefins limits their use in the applications where bondability (melt- or solvent-bonding) are highly desired. Thus there is a need for a compound which can be used as a single component or as an additive modifier in medical tubing application in the situations where durable connection is needed. For the connection of the tubing to the connectors, solvent bonding or welding is a preferred technique because of ease operation, strength and durability of the bond or weld. Also the compound needed for medical tubing requires extrudability, solvent bondability to the connectors, resistance to kinking, no odor, gamma radiation stability, chemical resistance to drugs flowing through the tubing, low extractables from the tubing, low leachables from the tubing, and non-tackiness after sterilization. For transfer of medicine fluid, clarity of the tube is also strongly preferred for monitoring the flow of the critical medicinal fluid.

The present invention solves some of these problems; namely, modified PP and its containing materials can be beneficially used (as a single component and as an additive compounds) to improve solvent bondability and overall compatibility of the PP and PP based TPEs with dissimilar plastic materials (PMMA, PC, MABs and etc.). Namely, by utilization modification technology that incorporates functional groups based on hybrid organic silane micromolecules in combination with the difunctional metallic diacrylate monomers, we are changing chemistry of PP and/or TPE matrix and subsequently hydrophilicity. Grafted functional groups are acting as compatibilizer networks between dissimilar materials and promoting respectively, solvent adhesion and melt interactions between interfaces.

Another application is smart medical devices & packaging with integrated microchips, cameras or sensors. As noted above modified PP and its containing materials can be also used in the applications where melt adhesion and compatibility are needed between PP based materials and dissimilar plastic or metal surfaces. One of the potential application is encapsulation of the readable tags and metal parts into components of the medical devices without chemical adhesives (for examples RFID, radio frequency identification— low, high, ultra-high frequency, microwave and other types of tags and sensors). Readable tags and sensors are offering numerous product enhancement opportunities and differentiation, particularly for auto identification and data capturing, however tags and sensors are made from the materials which are immiscible/incompatible with the PP based materials; for example RFID tags are made mainly from a polyethylene terephthalate (PETE) substrate; because of its chemical structure PETE is incompatible with other plastics, especially with PP which is one of the widely used plastic in the medical devices field. Insolubility of the two polymers will cause problems during molding and also structure of the molded parts can lead to problems such as shifting of the tag, an air bubble forming between PETE and PP films, warping due to differing shrink rate and other incomparability issues. Grafted functional groups into PP matrix are changing PP matrix chemistry and polarity and thus improving interfacial interaction between PP and PETE; modified PP technology resolves PETE/PP miscibility issues and gives an opportunity to incorporate readable tags into medical devices. Moreover, functionalized PP materials also show potential to resolve encapsulation issue of the metal components in the parts of medical devices which are made from PP and PP based TPE materials. Increased forces required for debonding modified PP and/or PP based TPE materials from the metal surfaces are supporting claims about ability of modified PP compounds to promote melt adhesion between dissimilar materials.

This disclosure addresses unmet PP and PP based materials needs in addition to industry gaps in replacing materials of concerns containing product (i.e. plasticized PVC) with products which meet manufacturing and product requirements.

The amphiphilic graft copolymers disclosed herein provide advantages and improvements over the prior art. Some graft-modified polyolefin resins are known from U.S. Pat. No. 9,150,674, which are mainly obtained by grafting, maleic acid, maleic anhydride, or a maleic acid ester, or by grafting other types of carboxylic or dicarboxylic acids and etc., to an olefin polymer or copolymer such as polyethylene, an ethylene copolymer, or polypropylene in an attempt to improve its adhesiveness. These conventional graft-modified resins, however, are low viscous resins and they do not exhibit sufficient shapability to mold the parts, or do not exhibit sufficient physical-mechanical properties.

The present modification technology allows for grafting of functional groups while maintaining moldability and key physical-mechanical properties through reinforcement with hybrid micromolecules and formation of long chain branches. Moreover, PP modification technology described herein utilizes hybrid organic silane micromolecules chemistry in combination with the difunctional metallic diacrylate monomers which clearly is different approach than any existing graft-modification technology discussed in the prior art.

The modified PP based on PP modification technology that utilizes hybrid organic silane micromolecules in combination with the difunctional metallic diacrylate monomer in the presence of a free-radical initiator is a novel approach utilizing highly reactive hydroscopic nature of the organic silane micromolecules to achieve hydrolyze process of the Si(OR)$_3$ groups using hydroxide groups of the oxide or hydroxide materials and formation of the hybrid structure via follow-up grafting process. Grafted functional groups in the modified PPs act as a compatibilizer network between dissimilar materials and promoting respectively solvent adhesion and melt interactions between interfaces. As a starting polymer, commercially available polypropylene homopolymers can used with melt values of 0.5-12 (g/10 min) range. Modification is done in the melt using twin screw extruder.

EMBODIMENTS

Various embodiments are listed below. It will be understood that the embodiments listed below may be combined with all aspects and other embodiments in accordance with the scope of the invention.

Embodiment 1

An amphiphilic copolymer comprising polypropylene and an inorganic-organic hybrid micromolecule, the amphiphilic copolymer, which is according to Formula (I):

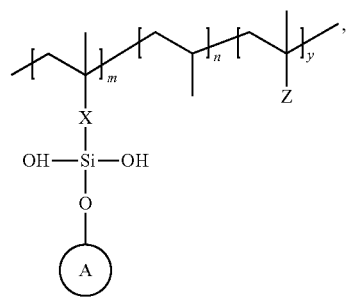

(I)

wherein X is an organic or an organo-functional group containing 1 to 6 carbons; A is a metal, an inorganic oxide, an inorganic hydroxide, or any other inorganic material; and n is in the range of about 78 to 99.9 mole percent; m is in the range of about 0.1 to 20 mole percent; the molar value of "y" is in the range of about 0 to 2.0 mole percent; and "Z", when y is greater than 0, comprises: M-X$_2$; XSiOR; or XSiOH, wherein "M-X$_2$" is an organo-metal salt and "OR" is an alkoxy group having 1 to 4 carbons.

Embodiment 2

The amphiphilic copolymer of embodiment 1, wherein the inorganic-organic hybrid micromolecule is a reaction product of an organo-silane and an inorganic oxide and/or hydroxide.

Embodiment 3

The amphiphilic copolymer of embodiment 1 or 2, wherein X is derived from a compound selected from the group consisting of epoxy, amino, acrylate, methacryloxy, and vinyl; and A is selected from the group consisting of: silicon, (Si), aluminum (Al), iron (Fe), titanium (Ti), silver (Ag), zinc (Zn), nickel (Ni), calcium (Ca), copper (Cu), tin (Sn); oxides thereof; hydroxides thereof; and mixtures of the foregoing.

Embodiment 4

The amphiphilic copolymer of one of embodiments 1 to 3, wherein the inorganic-organic hybrid micromolecule grafted to the polypropylene is a reaction product of an organo-functional silane with an inorganic oxide and/or hydroxide in solution, wherein a weight ratio of the organo-functional silane to the inorganic oxide and/or hydroxide is at least 10:1.

Embodiment 5

The amphiphilic copolymer of one of embodiments 1 to 4, wherein y is 0, and the amphiphilic copolymer is according to Formula (IA):

(IA)

[Structure: polymer backbone with repeating units m and n; side group X attached to OH—Si(—OH)—O—A]

Embodiment 6

The amphiphilic copolymer of embodiment 5, wherein X is derived from 3-(trimethoxysilyl)propyl methacrylate and the amphiphilic copolymer is according to Formula (VII):

(VII)

[Structure: polymer backbone with repeating units n and m; side group X with propyl linker to OH—Si(—OH)—O—A]

Embodiment 7

The amphiphilic copolymer of one of embodiments 1 to 6 wherein A is derived from $Si(OH)_4$ or $SiO_2$.

Embodiment 8

The amphiphilic copolymer of one of embodiments 1 to 7 having a melting point in the range of 140 to 180° C.

Embodiment 9

The amphiphilic copolymer of one of embodiments 1 to 8 having a capillary viscosity in the range of 100 to 300 Pa·s at $180$ $s^{-1}$.

Embodiment 10

The amphiphilic copolymer of one of embodiments 1 to 9 having a weight average molecular weight (Mw) in the range of about 100,000 to about 350,000 g/mol.

Embodiment 11

The amphiphilic copolymer of one of embodiments 1 to 10 having a dispersity index in the range of 1.5 to 9.

Embodiment 12

The amphiphilic copolymer of one of embodiments 1 to 11 having a long chain branching frequency in the range of 0.007 to 0.017 per 1000 carbon.

Embodiment 13

The amphiphilic copolymer of one of embodiments 1 to 12 having a melt flow rate in the range of 15 to 55 g/10 minutes.

Embodiment 14

A process for preparing an amphiphilic copolymer comprising: obtaining polypropylene; polymerizing the polypropylene with an inorganic-organic hybrid micromolecule in the presence of a co-reagent that comprises a metal organic salt to form the amphiphilic copolymer; wherein the amphiphilic copolymer comprises a polypropylene backbone and side-chains based on one or more organo-functional silanes.

Embodiment 15

The process of embodiment 14, wherein the amphiphilic copolymer is according to Formula (I):

(I)

[Structure: polymer backbone with repeating units m, n, and y; side group X attached to OH—Si(—OH)—O—A; Z substituent on y unit]

wherein X is an organic or an organo-functional group containing 1 to 6 carbons; A is a metal, an inorganic oxide, an inorganic hydroxide, or any other inorganic material; "n" is in the range of about 78 to 99.9 mole percent; m is in the range of about 0.1 to 20 mole percent; the molar value of "y" is in the range of about 0 to 2.0 mole percent; and "Z", when y is greater than 0, comprises: $M-X_2$; XSiOR; or XSiOH, wherein "$M-X_2$" is an organo-metal salt and "OR" is an alkoxy group having 1 to 4 carbons.

Embodiment 16

The process of embodiment 14 or 15, wherein the hybrid inorganic-organic micromolecule is synthesized via solution polymerization.

Embodiment 17

The process of embodiment 16, wherein the synthesis of the hybrid inorganic-organic micromolecule is performed at a reaction temperature in the range of 20° C. to 35° C.

Embodiment 18

The process of one of embodiments 14 to 17, wherein the hybrid inorganic-organic micromolecule is copolymerized with the polypropylene in the presence of the co-agent via melt or solution processing at a reaction temperature in the range of 150° C. to 250° C.

Embodiment 19

The process of one of embodiments 14 to 18, wherein the co-agents comprise an organo-metal salt based on difunctional diacrylate monomers.

Embodiment 20

A medical device formed from a blend comprising: a base polymeric formulation comprising at least a polymer or co-polymer of propylene; and an additive comprising a copolymer having a polypropylene backbone and hybrid micromolecule side-chains based on organo-functional silanes (PP-g-XSiOA), where "X" is an organic group or an organo-functional group; and "A" is a metal, an inorganic oxide, an inorganic hydroxide, or any other inorganic material; the PP-g-XSiOA being present in the blend in an amount in the range of about 0.01 to about 20.0% by weight of the blend.

Embodiment 21

The medical device of embodiment 20, wherein the PP-g-XSiOA is according to Formula (I):

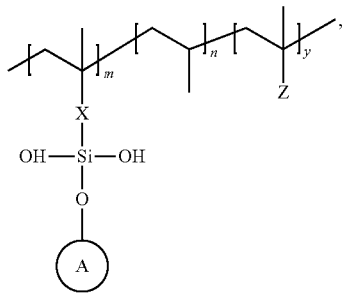

(I)

wherein X is an organic group or an organo-functional group; A is a metal, an inorganic oxide, an inorganic hydroxide, or any other inorganic material; and "n" is in the range of about 78 to 99.9 mole percent; m is in the range of about 0.1 to 20 mole percent; the molar value of "y" is in the range of about 0 to 2.0 mole percent; and "Z", when y is greater than 0, comprises: $M-X_2$; XSiOR; or XSiOH, wherein "$M-X_2$" is an organo-metal salt and "OR" is an alkoxy group having 1 to 4 carbons.

Embodiment 22

The medical device of embodiment 20 or 21, wherein the base polymeric formulation comprises polypropylene, a polyethylene-polypropylene co-polymer, a polypropylene-containing thermoplastic elastomer (TPE), or combinations thereof.

Embodiment 23

The medical device of one of embodiments 20 to 22, wherein X of the PP-g-XSiOA is derived from a compound selected from the group consisting of epoxy, amino, acrylate, methacryloxy, and vinyl; and A is selected from the group consisting of: silicon, (Si), aluminum (Al), iron (Fe), titanium (Ti), silver (Ag), zinc (Zn), nickel (Ni), calcium (Ca), copper (Cu), tin (Sn); oxides thereof; hydroxides thereof; and mixtures of the foregoing.

Embodiment 24

The medical device of one of embodiments 20 to 23, wherein the PP-g-XSiOA has a melting point in the range of 140 to 180° C.

Embodiment 25

The medical device of one of embodiments 20 to 24, wherein the PP-g-XSiOA has a capillary viscosity in the range of 100 to 300 Pa·s at 180 s$^{-1}$.

Embodiment 26

The medical device of one of embodiments 20 to 25, wherein the PP-g-XSiOA has a weight average molecular weight (Mw) in the range of about 100,000 to about 350,000 g/mol.

Embodiment 27

The medical device of one of embodiments 20 to 26, wherein the PP-g-XSiOA has a dispersity index in the range of 1.5 to 9.

Embodiment 28

The medical device of one of embodiments 20 to 27, wherein the PP-g-XSiOA has a long chain branching frequency in the range of 0.007 to 0.017 per 1000 carbon.

Embodiment 29

The medical device of one of embodiments 20 to 28, wherein the PP-g-XSiOA has a melt flow rate in the range of 15 to 55 g/10 minutes.

Embodiment 30

The medical device of one of embodiments 20 to 29, which has one or more improved characteristics relative to a comparative a base polymeric formulation without a PP-g-XSiOA additive selected from the group consisting of: laser printability and/or marking; solvent bonding, and melt adhesion to polar surfaces.

Embodiment 31

The medical device of one of embodiments 20 to 30 in the form of tubing.

Embodiment 32

A medical device comprising: a tubing comprising a polymeric blend comprising a base polymeric formulation comprising at least a polymer or co-polymer of propylene and an additive comprising a copolymer having a polypropylene backbone and hybrid micromolecule side-chains based on organo-functional silanes (PP-g-XSiOA), where "X" is an organic group or an organo-functional group; and "A" is a metal, an inorganic oxide, an inorganic hydroxide, or any other inorganic material; wherein the PP-g-XSiOA is present in the blend in an amount in the range of about 0.01 to about 20.0% by weight of the blend; and a connector bonded to the tubing.

Embodiment 33

The medical device of embodiment 32, wherein the PP-g-XSiOA is effective to enhance bonding of the tubing to the connector.

Embodiment 34

The medical device of one of embodiments 32 to 33, wherein the PP-g-XSiOA is according to Formula (I):

$$\underset{X}{\underset{|}{\underset{OH-Si-OH}{\underset{|}{\underset{O}{\underset{|}{A}}}}}} \text{(I)}$$

wherein X is an organic group or an organo-functional group; A is a metal, an inorganic oxide, an inorganic hydroxide, or any other inorganic material; and "n" is in the range of about 78 to 99.9 mole percent; m is in the range of about 0.1 to 20 mole percent; the molar value of "y" is in the range of about 0 to 2.0 mole percent; and "Z", when y is greater than 0, comprises: M-X2; XSiOR; or XSiOH, wherein "M-X2" is an organo-metal salt and "OR" is an alkoxy group having 1 to 4 carbons.

Embodiment 35

The medical device of one of embodiments 32 to 34, wherein the base polymeric formulation comprises polypropylene, a polyethylene-polypropylene co-polymer, a polypropylene-containing thermoplastic elastomer (TPE), or combinations thereof.

Embodiment 36

The medical device of one of embodiments 32 to 35, wherein X of the PP-g-XSiOA is derived from a compound selected from the group consisting of epoxy, amino, acrylate, methacryloxy, and vinyl; and A is selected from the group consisting of: silicon, (Si), aluminum (Al), iron (Fe), titanium (Ti), silver (Ag), zinc (Zn), nickel (Ni), calcium (Ca), copper (Cu), tin (Sn); oxides thereof; hydroxides thereof; and mixtures of the foregoing.

Embodiment 37

The medical device one of embodiments 32 to 36, wherein the PP-g-XSiOA has a melting point in the range of 140 to 180° C.

Embodiment 38

The medical device of one of embodiments 32 to 37, wherein the PP-g-XSiOA has a capillary viscosity in the range of 100 to 300 Pa·s at 180 s-1.

Embodiment 39

The medical device of one of embodiments 32 to 38, wherein the PP-g-XSiOA has a weight average molecular weight (Mw) in the range of about 100,000 to about 350,000 g/mol.

Embodiment 40

The medical device of one of embodiments 32 to 39, wherein the PP-g-XSiOA has a dispersity index in the range of 1.5 to 9.

Embodiment 41

The medical device of one of embodiments 32 to 40, wherein the PP-g-XSiOA has a long chain branching frequency in the range of 0.007 to 0.017 per 1000 carbon.

Embodiment 42

The medical device of one of embodiments 32 to 41, wherein the PP-g-XSiOA has a melt flow rate in the range of 15 to 55 g/10 minutes.

Embodiment 43

The medical device of one of embodiments 32 to 42, wherein the connector comprises a metal.

Embodiment 44

The medical device of embodiment 43, wherein the metal is selected from the group consisting of: steel, cobalt, titanium, tantalum, and their alloys.

Embodiment 45

The medical device of one of embodiments 32 to 44, wherein the connector is melt-bonded to the tubing.

Embodiment 46

The medical device of one of embodiments 32 to 42, wherein the connector comprises a polar material.

Embodiment 47

The medical device of embodiment 46, wherein the polar material is selected from the group consisting of: poly (methyl methacrylate) (PMMA), styrene maleic anhydride (SMA), polycarbonate (PC), and methyl methacrylate-acrylonitrile-butadiene-styrene (MABS).

Embodiment 48

The medical device of one of embodiments 32 to 42 or 46 to 47, wherein the connector is solvent-bonded to the tubing.

Embodiment 49

A method of making a medical device comprising: obtaining a copolymer having a polypropylene backbone and hybrid micromolecule side-chains based on organo-functional silanes (PP-g-XSiOA), where "X" is an organic group or an organo-functional group; and "A" is a metal, an inorganic oxide, an inorganic hydroxide, or any other inorganic material; combining the PP-g-XSiOA with a base polymeric formulation comprising at least a polymer or co-polymer of propylene to form a blend, the PP-g-XSiOA being present in the blend in an amount in the range of about 0.01 to about 20.0% by weight of the blend; forming a tubing from the blend; and bonding the tubing to a connector in the absence of an adhesive to form the medical device.

Embodiment 50

The method of embodiment 49, wherein the PP-g-XSiOA is according to Formula (I):

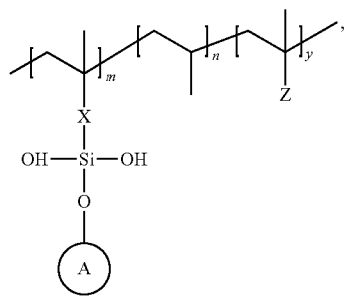

wherein X is an organic group or an organo-functional group; A is a metal, an inorganic oxide, an inorganic hydroxide, or any other inorganic material; and "n" is in the range of about 78 to 99.9 mole percent; m is in the range of about 0.1 to 20 mole percent; the molar value of "y" is in the range of about 0 to 2.0 mole percent; and "Z", when y is greater than 0, comprises: M-X2; XSiOR; or XSiOH, wherein "M-X2" is an organo-metal salt and "OR" is an alkoxy group having 1 to 4 carbons.

Embodiment 51

The method of one of embodiments 49 to 50, wherein the connector comprises a metal.

Embodiment 52

The method of embodiment 51, wherein the metal is selected from the group consisting of: steel, cobalt, titanium, tantalum, and their alloys.

Embodiment 53

The method of one of embodiments 49 to 52, wherein the connector is melt-bonded to the tubing.

Embodiment 54

The method of one of embodiments 49 to 50, wherein the connector comprises a polar material.

Embodiment 55

The method of embodiment 54, wherein the polar material is selected from the group consisting of: poly(methyl methacrylate) (PMMA), styrene maleic anhydride (SMA), polycarbonate (PC), and methyl methacrylate-acrylonitrile-butadiene-styrene (MABS).

Embodiment 56

The method of one of embodiments 54 to 55, wherein the connector is solvent-bonded to the tubing.

EXAMPLES

The following materials were used for synthesis of amphiphilic graft copolymers PP-g-XSiOA and comparative polymers.

Organic silane: 3-(Trimethoxysilyl)propyl methacrylate (synonym: [3-(Methacryloyloxy)propyl]trimethoxysilane) obtained from Sigma-Aldrich.

Silica (synonyms: silica, silicic anhydride, silicon dioxide amorphous, silicon dioxide) and aluminum oxyhydroxide (AlO(OH)) having average particle size 0.1-0.5 μm (aggregate), obtained both from Sigma-Aldrich.

LUPEROX 101: (synonym: 2,5-Bis(tert-butylperoxy)-2,5-dimethylhexane; 2,5-Bis(tert-butylperoxy)-2,5-dimethylhexane) obtained from Sigma-Aldrich.

Polypropylene (PP): commercial grade 13 melt flow (MF) PP homopolymer (made by a Ziegler-Natta catalyst); melt flow of the PP was 3.6 g/10 minutes (measured at 230° C. and 2.16 kg weight—ASTM method D1238-13.

Co-agent difunctional zinc dimethacrylate: (synonyms: zinc methacrylate and methacrylic acid zinc salt) obtained from Sigma-Aldrich.

Example 1

Polymers were synthesized according to the formulations of Table 1 in weight % with respect to the polypropylene (PP) content. Formulations 5-7 were inventive as modifications of base polypropylene.

TABLE 1

| | Component wt.-% | | | | |
|---|---|---|---|---|---|
| | PP | Peroxide | Monomer 1[a] | Monomer 2[b] | Co-agent |
| Formulation 1 Comparative | 100 | 0 | 0 | 0 | 0 |
| Formulation 2 Comparative | 100 | 0.25 | 0 | 0 | 0 |
| Formulation 3 Comparative | 100 | 0.25 | 1 | 0 | 0 |
| Formulation 4 Comparative | 100 | 0.25 | 0 | 0 | 1.0 |
| Formulation 5 | 100 | 0.25 | 0 | 0.5 | 0.2 |

TABLE 1-continued

| | Component wt.-% | | | | |
|---|---|---|---|---|---|
| | PP | Peroxide | Monomer 1[a] | Monomer 2[b] | Co-agent |
| Formulation 6 | 100 | 0.25 | 0 | 1 | 0.2 |
| Formulation 7 | 100 | 0.25 | 0 | 1.5 | 0.2 |

[a]Neat 3-(Trimethoxysilyl)propyl methacrylate
[b]Hybrid micromolecule synthesized based on silica + 3-(Trimethoxysilyl)propyl methacrylate Synthesis experiments were performed on a ZSK 30 mm twin screw extruder. To avoid degradation/oxidation experiments were done under $N_2$ blanket. Before extrusion experiments, reaction components such as PP, monomers, co-agents and peroxide were blended together using Henschel automated mixing equipment. Blended mixture of the reaction components was fed to the extruder from the main feeder. Table 2 summarizes conditions of the extrusion process.

TABLE 2

| | Condition | | |
|---|---|---|---|
| | Torque % | Extruder RPM | Melt Temperature (° F.) |
| Formulation 1 Comparative | 60 | 266 | 478 |
| Formulation 2 Comparative | 37 | 262 | 449 |
| Formulation 3 Comparative | 36 | 262 | 414 |
| Formulation 4 Comparative | 35 | 261 | 422 |
| Formulation 5 | 38 | 260 | 421 |
| Formulation 6 | 31 | 260 | 422 |
| Formulation 7 | 31 | 258 | 460 |

Example 2

Testing
Differential Scanning Calorimetry (DSC).

Two heating steps and one cooling step were performed for each sample under −20 to 200° C. temperature range, using 10° C./min heating rate. Collected DSC thermograms were used to calculate melting, crystallization temperatures and degree of crystallinity.

Figure 2:
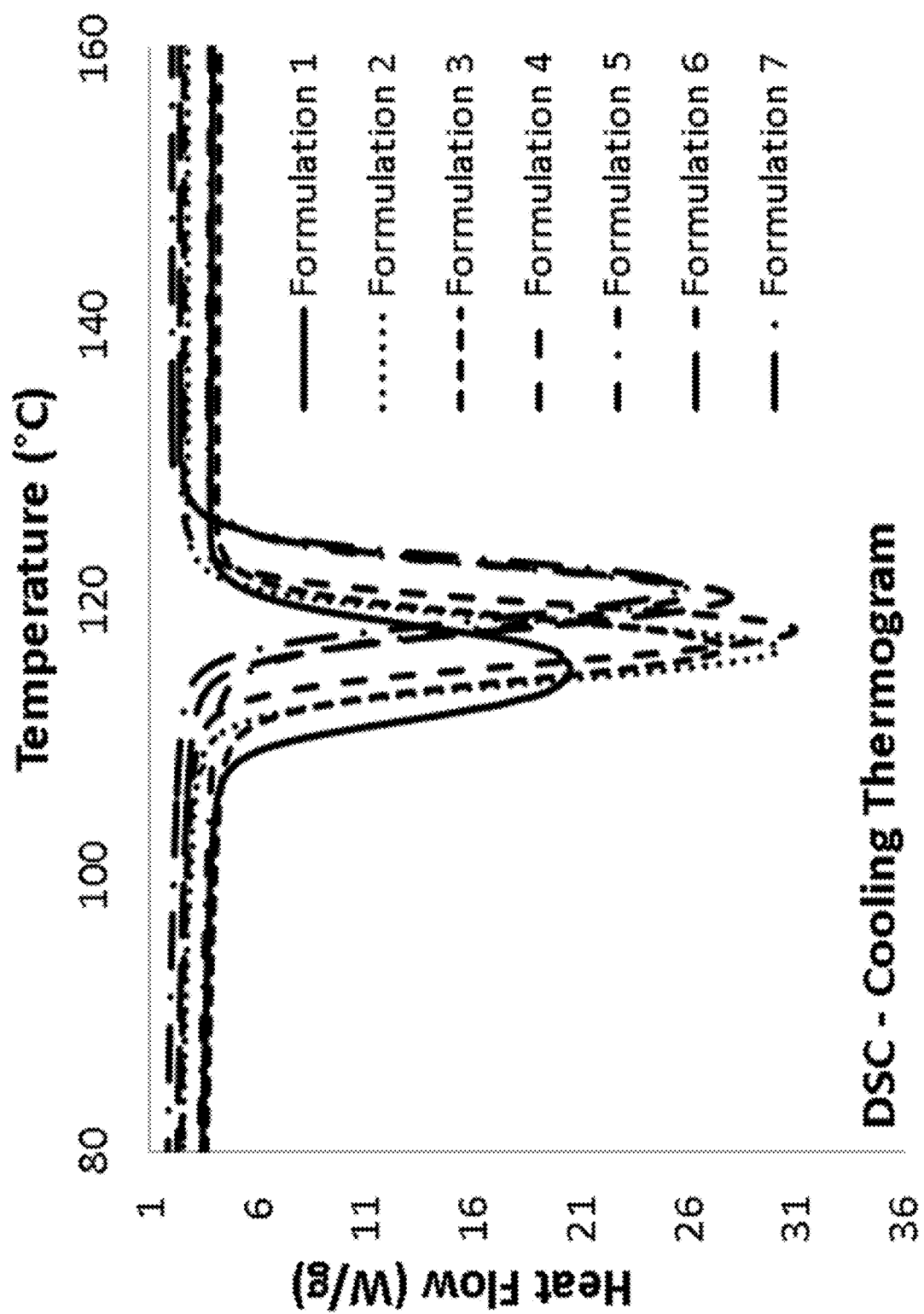
FIG. 2 is a thermogram of heat flow (W/g) for polymers according to formulations 1-7 versus temperature (° C.) for a second range of temperatures during a cooling.

FIG. 1 is a thermogram of heat flow (W/g) for the synthesized polymers according to formulations 1-7 versus temperature (° C.) for a first range of temperatures during a second heating. FIG. 2 is a thermogram of heat flow (W/g) for polymers according to formulations 1-7 versus temperature (° C.) for a second range of temperatures during a cooling. Table 3 shows crystallization temperatures ($T_{c\text{-}PP}$). Table 3 also shows melting points ($T_m$) and % crystallinity after the second heating step.

TABLE 3

| Sample Name | $T_{c\text{-}PP}$ (° C.) | $T_m$ (° C.) | Crystallinity[a] % |
|---|---|---|---|
| Formulation 1 | 115.0 | 164.3 | 44.4 |
| Comparative Formulation 2 | 117.8 | 163.1 | 54.6 |
| Comparative Formulation 3 | 116.5 | 162.4 | 47.9 |

TABLE 3-continued

| Sample Name | $T_{c\text{-}PP}$ (° C.) | $T_m$ (° C.) | Crystallinity[a] % |
|---|---|---|---|
| Comparative Formulation 4 | 117.8 | 163.1 | 54.6 |
| Comparative Formulation 5 | 120.5 | 163.8 | 46.4 |
| Formulation 6 | 120.2 | 163.9 | 52.6 |
| Formulation 7 | 120.9 | 163.5 | 53.2 |

[a]Degree of crystallinity (%) = ($\Delta H_m/\Delta H_{mo}$) × 100
$\Delta H m_0$ is a reference value and represents the heat of melting of "100% crystalline" polymer. $\Delta H m_0$ of 100% crystalline PP is 207.1 (J/g)

In light of Table 3, the modification process does not significantly affect melting temperature and degree of crystallinity. That is, the synthesized graft copolymers show melting temperatures and degree of crystallinity comparable to those of the base/unmodified polypropylene. Crystallization temperature ($T_{c\text{-}PP}$) increased by 2-6° C. for synthesized graft copolymers relative to the base/unmodified polypropylene.

Melt Flow Rate (MFR).
ASTM 1238-13 method was used for melt flow rate (MFR) measurement at 230° C. using 2.16 kg weight. Table 4 provides the MFR for formulations 1-7.

TABLE 4

| Sample Name | MFR g/10 minutes |
|---|---|
| Formulation 1 Comparative | 3.5 |
| Formulation 2 Comparative | 218.0 |
| Formulation 3 Comparative | 53.4 |
| Formulation 4 Comparative | 47.6 |
| Formulation 5 | 41.9 |
| Formulation 6 | 25.3 |
| Formulation 7 | 35.2 |

Table 4 shows that the modification process significant affected melt flow rate. MFR data shows that incorporation of monomers (either neat organic silanes or hybrid micromolecules+co-agent) in the polymer matrix decreases melt flow rate in the presence of peroxide, which is an indication that radical grafting reaction took place for all the formulations resulting in decreased MFR values relative to unmodified polypropylene (Formulation 2). In Formulation 2, MFR increased from 3.5 to 218 due to peroxide cracking.

Formulations 5, 6, and 7 show the lower MFR compared to Formulations 3-4, which is an indication that incorporation of the hybrid micromolecule monomers provided a higher degree of grafting. Formulation 6, which used 1.2 wt.-% modifier (monomer 2+co-agent) seems to have the lowest melt flow rate (MFR).

Capillary Viscosity.
Capillary viscosity measurements were performed at 220° C. at 500-8000 (1/s) shear rate.

TABLE 5

| | Viscosity (Pa · s) at Shear Rate (1/s) | | | |
|---|---|---|---|---|
| Sample Name | 90 | 180 | 360 | 7200 |
| Formulation 1 Comparative | 677 | 445 | 284 | 33 |

TABLE 5-continued

| | Viscosity (Pa · s) at Shear Rate (1/s) | | | |
|---|---|---|---|---|
| Sample Name | 90 | 180 | 360 | 7200 |
| Formulation 2 Comparative | 46 | 49 | 43 | 13 |
| Formulation 3 Comparative | 175 | 141 | 108 | 19 |
| Formulation 4 Comparative | 166 | 142 | 108 | 18 |
| Formulation 5 | 191 | 152 | 115 | 20 |
| Formulation 6 | 293 | 221 | 158 | 25 |
| Formulation 7 | 224 | 170 | 128 | 22 |

Capillary viscosity at lower shear rate shows the same trends as MFR data. Modification process has significant effect on the viscosity. For Formulation 2, viscosity decreased from 677 Pa·s to 46 Pa·s due to peroxide cracking.

Viscosity data from the dynamic rheology (at lower shear ~90 s$^{-1}$ shows that compare to peroxide cracked PP resin, incorporation of the monomers (monomer+co-agent) in the polymer matrix increases the viscosity from 46 Pa·s up to 293 Pa·s; that means that radical grafting reaction takes place for all the formulations which increases viscosity values.

Formulations 5, 6, and 7 show the highest viscosity that means that incorporation of both monomer+co-agent provide higher degree of grafting (even under high shear rate modified samples maintain higher viscosity then cracked PP).

Similar to MFR data, Formulation 6 has highest viscosity (for example, even under high shear rate, 7200 Pa·s, Formulation 6 maintains 2 times higher amount of viscosity then peroxide cracked PP). Formulation 6 provides excellent capillary rheology and MFR behavior.

Fourier Transform Infrared Spectroscopy (FTIR).

Figure 3:
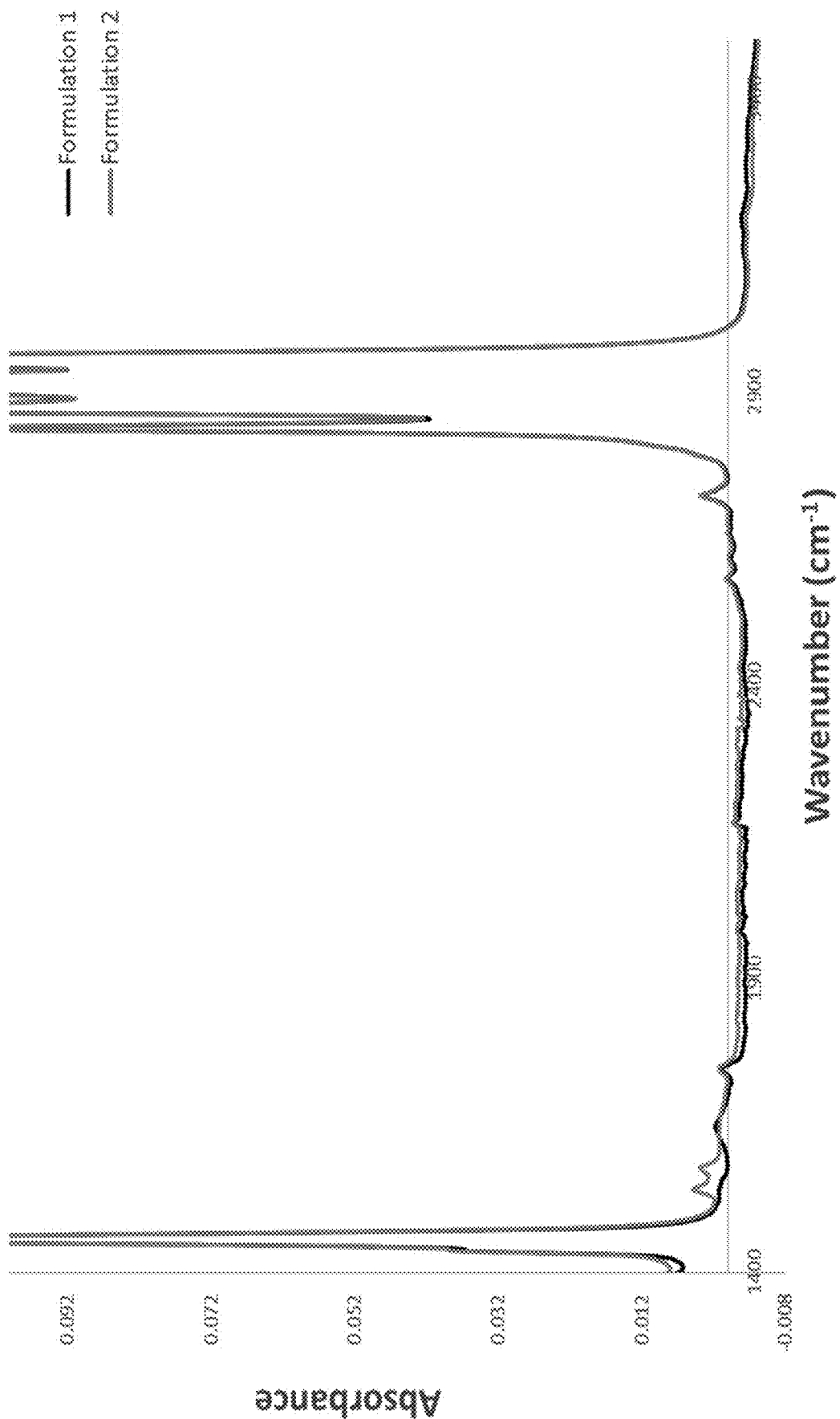
FIG. 3 provides FTIR spectra of Formulations 1-2.
Figure 4:
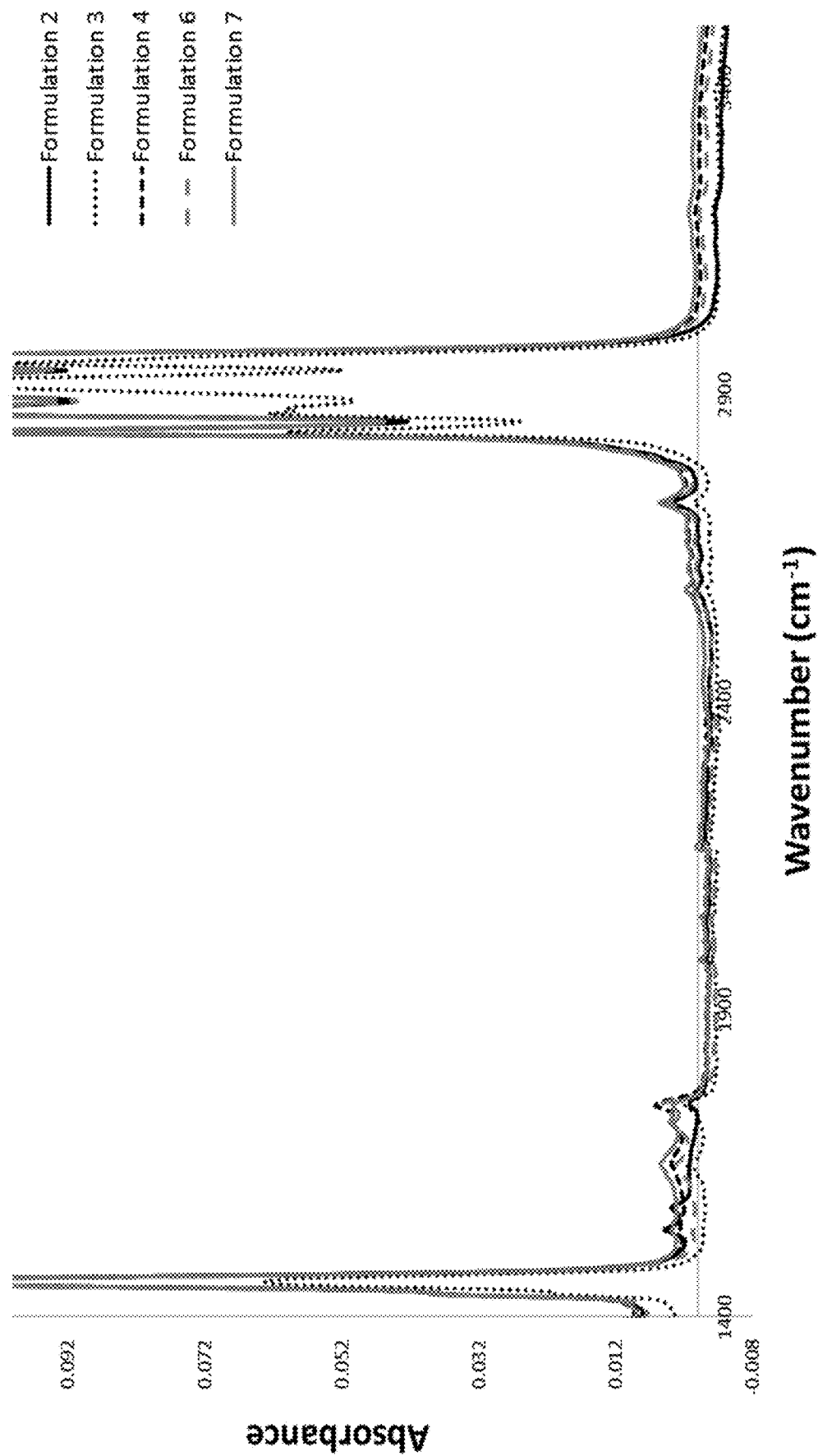
FIG. 4 provides FTIR spectra of Formulations 2-7 in 1400 to 3500 $cm^{-1}$ range.
Figure 5:
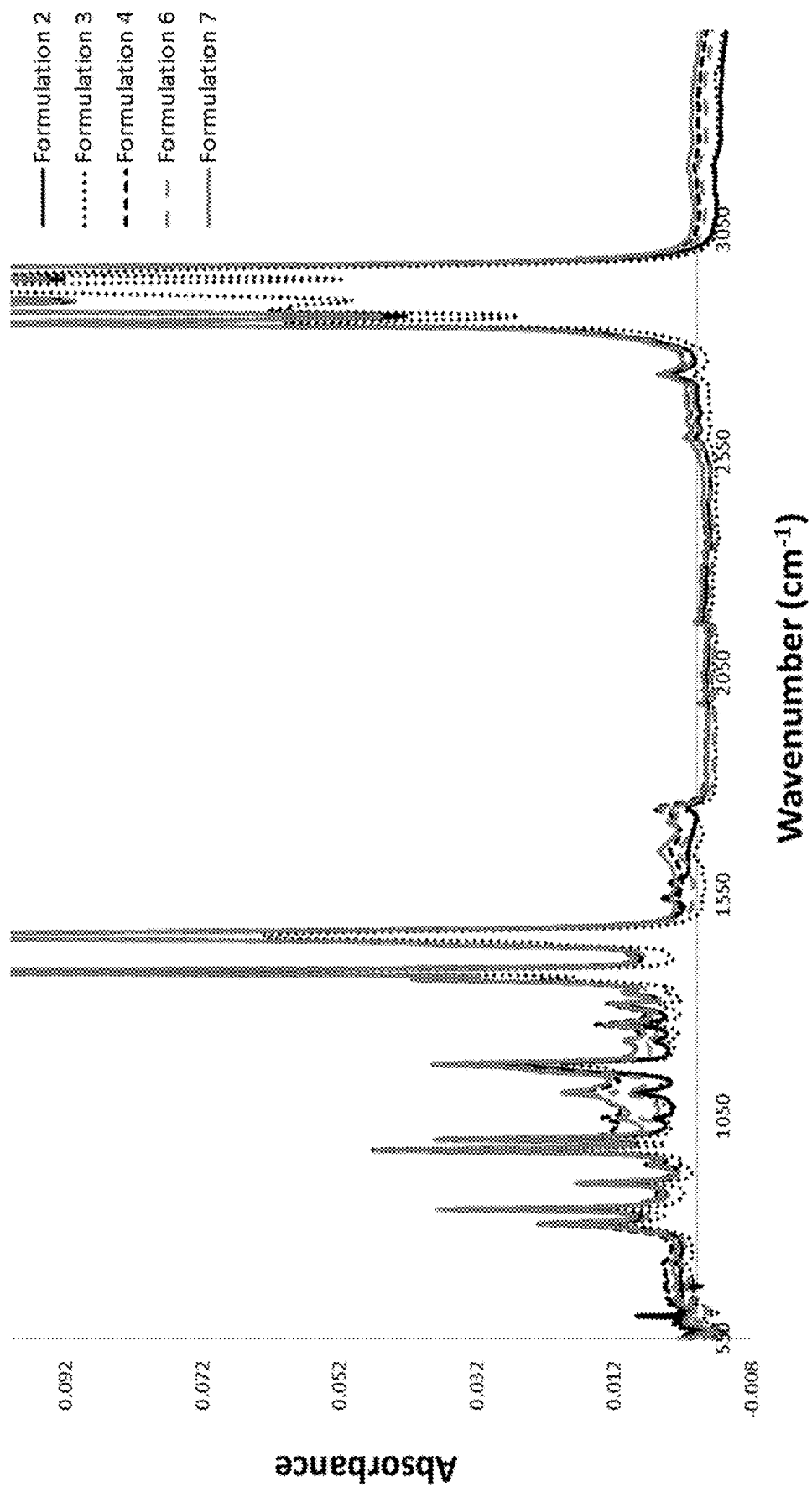
FIG. 5 provides FTIR spectra of Formulations 2-7 in 550 to 3500 $cm^{-1}$ range.
Figure 6:
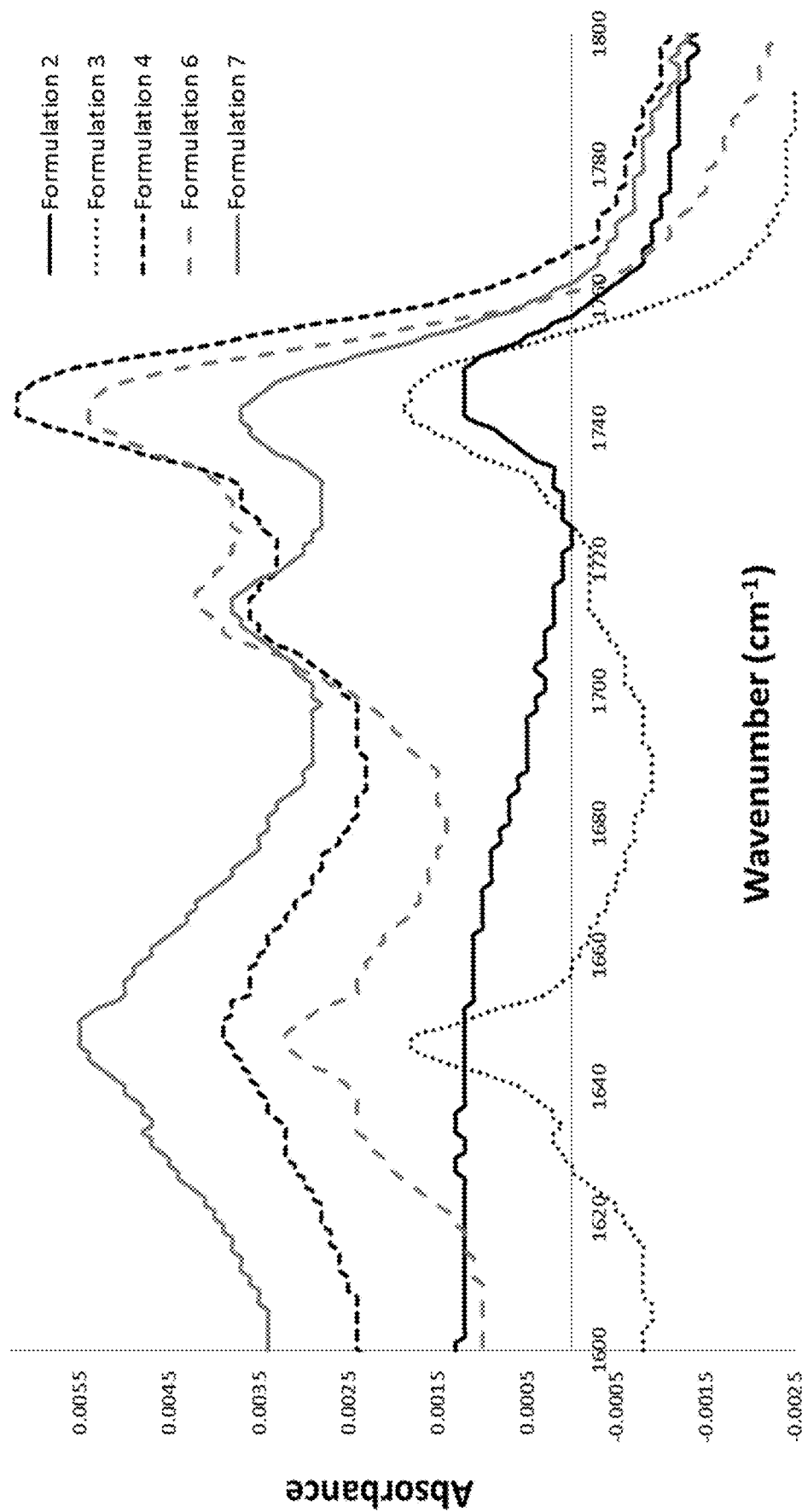
FIG. 6 provides FTIR spectra of Formulations 2-7 in 1600 to 1800 $cm^{-1}$ range.
Figure 7:
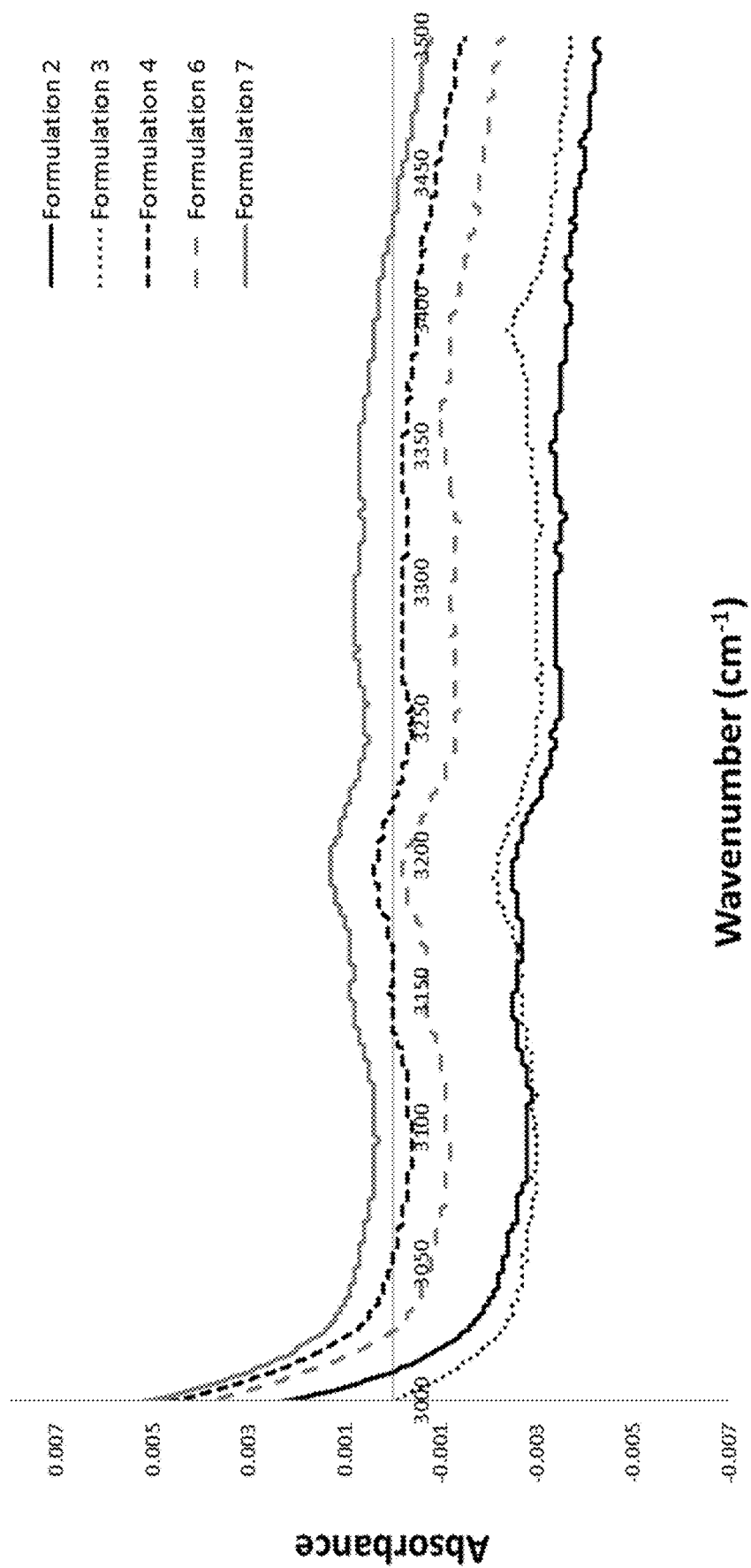
FIG. 7 provides FTIR spectra of Formulations 2-7 in 3000 to 3500 $cm^{-1}$ range.
Figure 8:
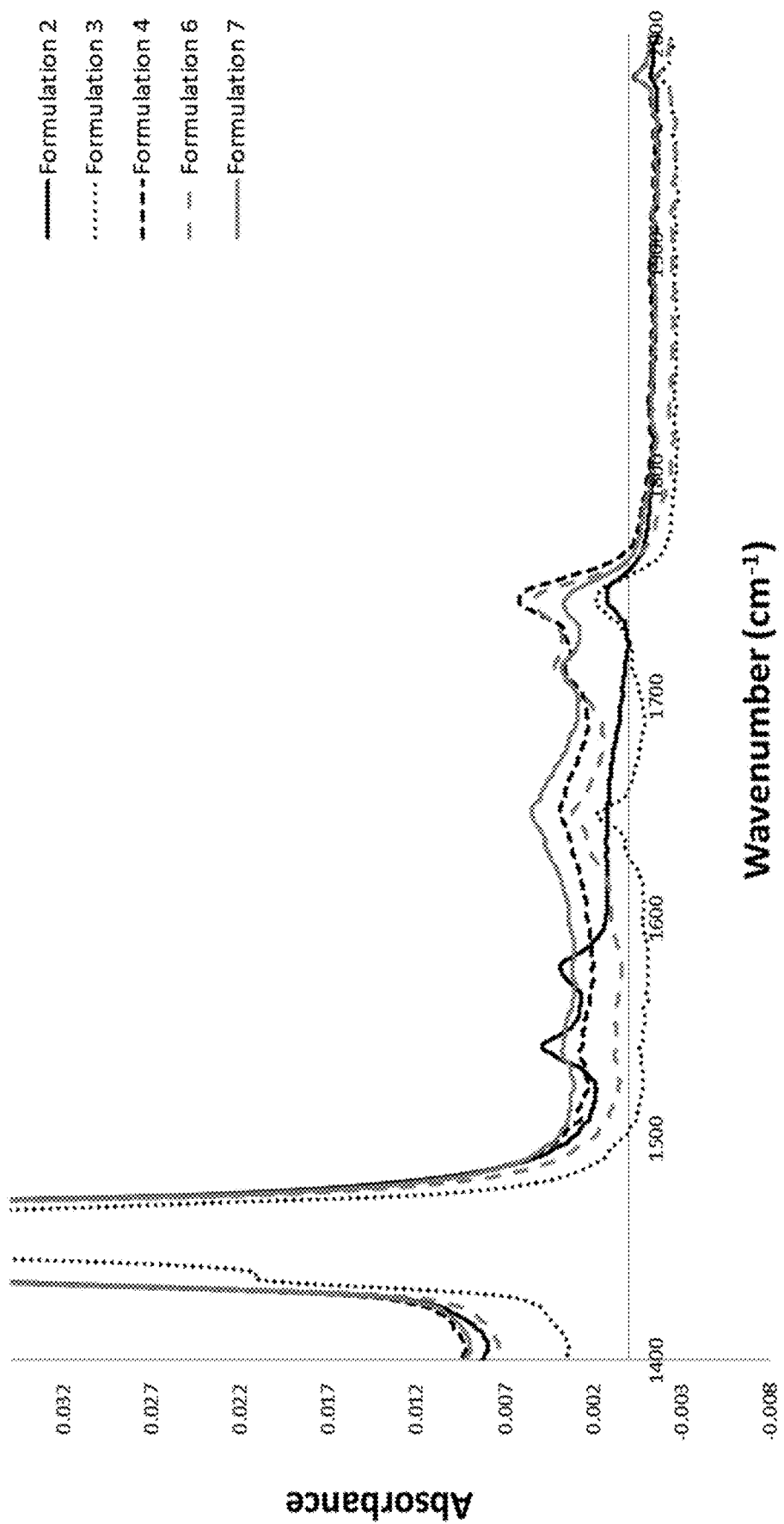
FIG. 8 provides FTIR spectra of Formulations 2-7 in 1400 to 2800 $cm^{-1}$ range.

FTIR spectra were collected in 550-4000 cm$^{-1}$ range using 32 scans. FIG. 3 provides FTIR spectra of Formulations 1-2. Formulation 2 shows appearance of C=C stretch at 1540-1580 cm$^{-1}$ after peroxide cracking (double peak). FIG. 4 provides FTIR spectra of Formulations 2-7 in 1400 to 3500 cm$^{-1}$ range. C=C stretch at 1540-1580 cm$^{-1}$ is not visible after modification due to consumption of C=C bands. FIG. 5 provides FTIR spectra of Formulations 2-7 in 550 to 3500 cm$^{1}$ range. Formation of new peaks were observed after the modification; new peaks correspond to carbonyl groups (C=O) at 1500-1800 cm$^{-1}$ from the monomer modifier. At 3000-3500 cm$^{-1}$ IR range intensity of the peaks which correspond to —OH groups are increased after the modification. FIG. 6 provides FTIR spectra of Formulations 2-7 in 1600 to 1800 cm$^{-1}$ range, which is an enlargement of what was observed in FIG. 5. In modified PP formulations, formation of new peaks at 1600-1800 cm$^{-1}$ range were observed; again, new peaks correspond to carbonyl groups (C=O) which are incorporated into modified PP from the monomer modifier. FIG. 7 provides FTIR spectra of Formulations 2-7 in 3000 to 3500 cm$^{-1}$ range, which is an enlargement of what was observed in FIG. 5. Again, at 3000-3500 cm$^{-1}$ IR range intensity of the peaks which are corresponding to —OH groups are increased after the modification, which indicates grafting of polar groups after the modification. FIG. 8 provides FTIR spectra of Formulations 2-7 in 1400 to 2800 cm$^{-1}$ range, which is an enlargement of what was observed in FIG. 5 and a broader perspective of FIG. 6, where new peaks corresponding to carbonyl groups (C=O) are shown in 1600-1800 cm$^{-1}$ range.

Gel Permeation Chromatography (GPC).

A GPC IR+Visco system was used, with TCB solvent (containing 300 ppm BHT stabilizer) at 1 mL/min, using 3 columns (300×7.5 mm (13 microns)), at 160° C., 200 µL injection volume, and 55 min run time. Samples were dissolved in TCB. Molecular mass distribution and molecular averages were based on a conventional calibration curve of third order made with 15 narrow polystyrene standards of known molecular weight (12200K g/mol to 672 g/mol). A factor Q was applied to transform polystyrene values to PP values. Universal calibration: When viscometer is used the molecular mass averages are calculated also with the universal calibration curve and they are named as (UC). UC is based on the concept of hydrodynamic volume; the basic principle behind GPC is that macromolecules are separated on the basis of their hydrodynamic radius or volume. Therefore, in the universal calibration a relationship is made between the hydrodynamic volume and the retention volume, instead of the relationship between molecular weight (MW) and elution volume used in the conventional calibration. The universal calibration theory assumes that two different macromolecules will have the same elution volume if they have the same hydrodynamic volume when they are in the same solvent and at the same temperature. Using this principle and the constants K and a from the Mark-Houwink-Sakurada equation it is possible to obtain the absolute MW of an unknown polymer.

Table 6 provides molecular weight data summary based on conventional calibration.

TABLE 6

Molecular Weight Data Summary Based on Conventional Calibration

| Sample Name | Mw (g/mol) | Mn (g/mol) | Mw/Mn Dispersity | Mz (g/mol) |
|---|---|---|---|---|
| Formulation 1 Comparative | 392,100 | 55,200 | 7.1 | 1,230,200 |
| Formulation 2 Comparative | 126,400 | 36,400 | 3.5 | 238,700 |
| Formulation 3 Comparative | 171,500 | 42,600 | 4.0 | 340,400 |
| Formulation 4 Comparative | 172,300 | 42,700 | 4.0 | 347,600 |
| Formulation 5 | 191,200 | 42,900 | 4.5 | 461,300 |
| Formulation 6 | 212,800 | 46,900 | 4.5 | 487,300 |
| Formulation 7 | 193,100 | 46,100 | 4.2 | 463,900 |

Mw is weight average molecular weight.
Mn is number average molecular weight.
Mz is z-average molecular weight.

Modification process has significant effects on the molecular weight (Mw) and its distribution (MWD). Due to the peroxide cracking for Formulation 2, Mw decreased ~3 times and provides the largest change of high molecular chain side, namely Mz value decreased almost 5 times.

After incorporation of the monomers/modifiers Mw and MWD increased as shown by Formulation 3-7.

Similar to MFR data Formulations 5, 6, and 7 show the highest Mw, Mn, and Mz values, which means that incorporation of both monomer and co-agent is provide higher degree of modification. Formulation 6 has highest Mz and Mw values; amount of monomer+co-agent content increases Mw and broadens MWD; namely Mz value of Formulation 5-7 is ~2 times higher than Mz of unmodified Formulation 2.

Long Chain Branching Calculation. The value of LCB from Viscometer has been calculated from a Mark-Houwink plot and the value used to transform g in g' has been of 0.9 units. Table 7 provides LCB calculations.

TABLE 7

| Sample Name | LCBf/1000° C. From Viscometer |
|---|---|
| Formulation 1 Comparative | 0 |
| Formulation 3 Comparative | 0.007 |
| Formulation 4 Comparative | 0.007 |
| Formulation 5 | 0.015 |
| Formulation 6 | 0.015 |
| Formulation 7 | 0.017 |

Table 7 shows that there is not a significant number of LCB frequency per 1000 carbon in the modified samples (Formulations 3 through 7); technology disclosed in this invention does not produce high melt strength long chain branched polyolefins and amphiphilic modification only leads formation of LCB with low frequency to 0.007 to 0.017. However, among prepared samples highest amount of LCBs where found in the samples produced by combination of the both monomer+co-agent modifiers—incorporation of 2 monomers shows formation of 2 times higher LCB numbers then Formulations 3 & 4 which are produced with single monomer.

Example 3

Blends of PP and amphiphilic graft copolymers and comparative formulations according to Table 1 were prepared in pellet form at 220° C. using a Rheomex OS 16 mm twin screw extruder from Thermo Fisher Scientific. The blend compositions are provided in Table 8. Obtained pellets were used to prepare polymer films with 3.000 inches×6.000 inches dimensions and 0.100 inch thickness using Carver compression molding machine at 200° C. temperature.

TABLE 8

| | Composition (wt. %) | |
|---|---|---|
| Sample Name | 80 | 20 |
| BF1-COMP-20 | PP | Formulation 1 -Comparative |
| BF2-COMP-20 | PP | Formulation 2 -Comparative |
| BF3-COMP-20 | PP | Formulation 3 - Comparative |
| BF4-COMP-20 | PP | Formulation 4 -Comparative |
| BF5-20 | PP | Formulation 5 |
| BF6-20 | PP | Formulation 6 |
| BF7-20 | PP | Formulation 7 |

Metal substrates to perform melt adhesion were rigid substrates having a material of Mild Steel A366/1008 with dimensions of 0.078 inches×3.000 inches×6.000 inches.

Example 4

Testing

Effects of amphiphilic graft copolymers on melt adhesion of flexible substrates onto metal substrates were analyzed. Samples for melt adhesion were prepared by placing polymer film on the metal substrate at room temperature and applying afterwards 0.01 tons of constant pressure at 200° C. temperature using Carver compression molding machine.

Melt Flow Rate (MFR).

ASTM 1238-13 method was used for melt flow rate (MFR) measurement at 230° C. using 2.16 kg weight.

Melt Adhesion Force Measurements.

Adhesion force was measured using a 90 degree peel test. Tests were performed using Instron 5965 with 5 kN load cell and 90 degree peel test fixture; test speed was 12 in/min and sample width was set to 1.2 inches. A peel test is performed between two substrates bonded together. The substrates may be both flexible or one may be flexible while the other is rigid. Generally the goal of a peel test is to determine the strength of the bond between two materials. This bonding strength may be referred to as the "stickiness" of a material as it is a measure of the samples resistance to separation from one another. This measured value may then be used to determine if the bond is strong enough or whether a different bonding process or promoter is needed. The 90 degree test requires a 90 degree peel test fixture to determine the bonding strength between a flexible and rigid substrate, where the plate lies horizontally with the gripped end of the tape sticking up perpendicular while the rest is bonded to the plate so that it forms an "L" shape.

Table 9 summarizes the melt adhesion results, where 10 specimens were tested for each sample and results were averaged.

TABLE 9

| Sample Name | Maximum Force (N) | Standard Deviation |
|---|---|---|
| BF1-COMP-20 | 0 | N/A |
| BF2-COMP-20 | 0 | N/A |
| BF3-COMP-20 | 32.61 | 8.26 |
| BF4-COMP-20 | 18.45 | 3.66 |
| BF5-20 | 66.3 | 5.45 |
| BF6-20 | 92.2 | 2.08 |
| BF7-20 | 58.79 | 5.58 |

Figure 10:
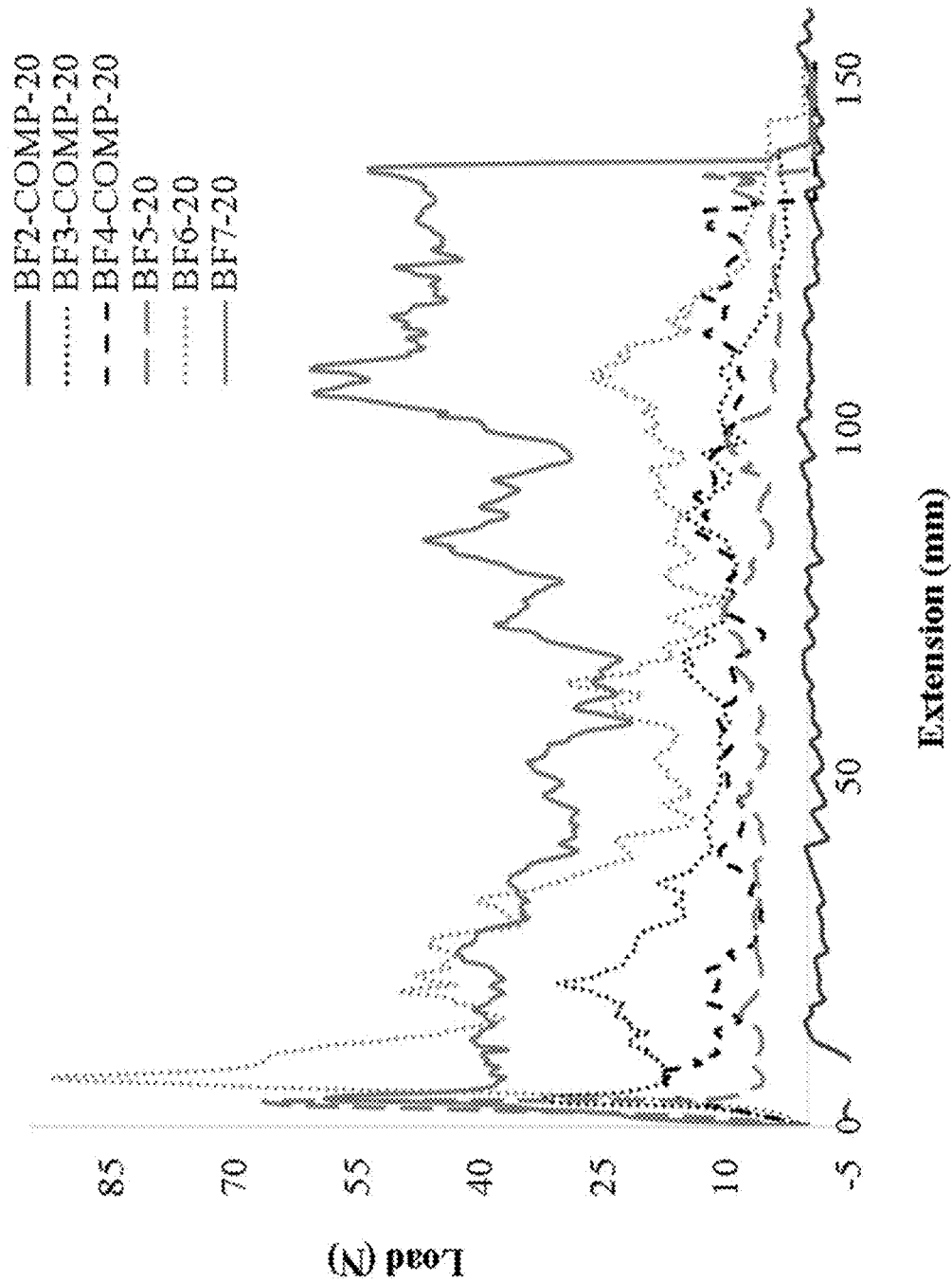
FIG. 10 is a graph of load (N) versus extension (mm) for adhesion force measurements for polypropylene and amphiphilic graft copolymers compositions melt-adhered to metal substrates.

FIG. 10 is a graph of load (N) versus extension (mm), showing effects of 20 wt. % amphiphilic graft copolymer (BF5-20, BF6-20, BF7-20) addition on the melt adhesion behavior of PP on the metal substrate in comparison with PP performance with 20 wt. % comparative formulations (BF2-COMP-20, BF3-COMP-20, BF4-COMP-20). As seen from the graphs amphiphilic graft copolymers improves melt adhesion of PP on the metal surface which subsequently result higher maximum and averaged debonding forces across the metal substrate than PP samples with 20 wt. % comparative formulations.

Example 5

Testing

Effects of concentration of amphiphilic graft copolymers (wt. %) on melt adhesion of flexible substrates onto metal substrates were analyzed. The blend compositions are provided in Table 10, where Formulation 6 of Table 1 was used.

TABLE 10

| | Composition (wt. %) | |
|---|---|---|
| Sample Name | PP | FORMULATION 6 |
| BF6-0 | 100 | 0 |
| BF6-0.5 | 99.5 | 0.5 |
| BF6-1 | 99 | 1 |
| BF6-5 | 95 | 5 |
| BF6-10 | 90 | 10 |
| BF6-20 | 20 | 20 |

Melt adhesion was measured as discussed in Example 4. Table 11 summarizes the melt adhesion results, where 10 specimens were tested for each sample and results were averaged.

TABLE 11

| Sample Name | Maximum Force (N) | Standard Deviation |
| --- | --- | --- |
| BF6-0 | 0 | N/A |
| BF6-0.5 | 13.81 | 3.11 |
| BF6-1 | 33.46 | 5.06 |
| BF6-5 | 55.50 | 4.01 |
| BF6-10 | 88.02 | 3.66 |
| BF6-20 | 92.2 | 2.08 |

Figure 11:
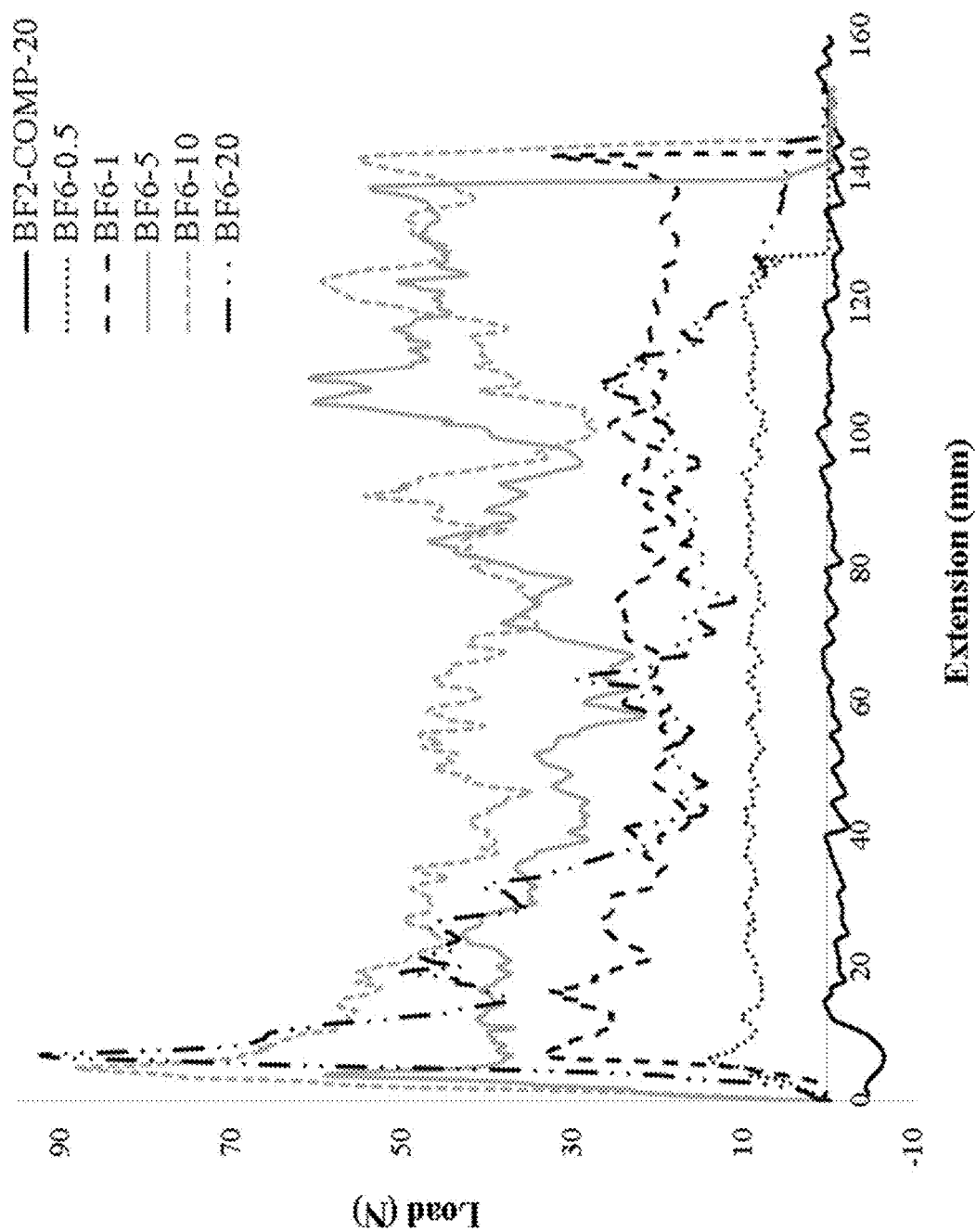
FIG. 11 is a graph of load (N) versus extension (mm) for adhesion force measurements for polypropylene and amphiphilic graft copolymers compositions melt-adhered to metal substrates.

FIG. 11 is a graph of load (N) versus extension (mm), showing effects of amphiphilic graft copolymer concentration on the melt adhesion behavior of PP across metal substrate. Amphiphilic graft copolymer improves melt bonding of PP on the metal surface even at low 0.5 wt. % concentration level.

Example 6

Figure 12:
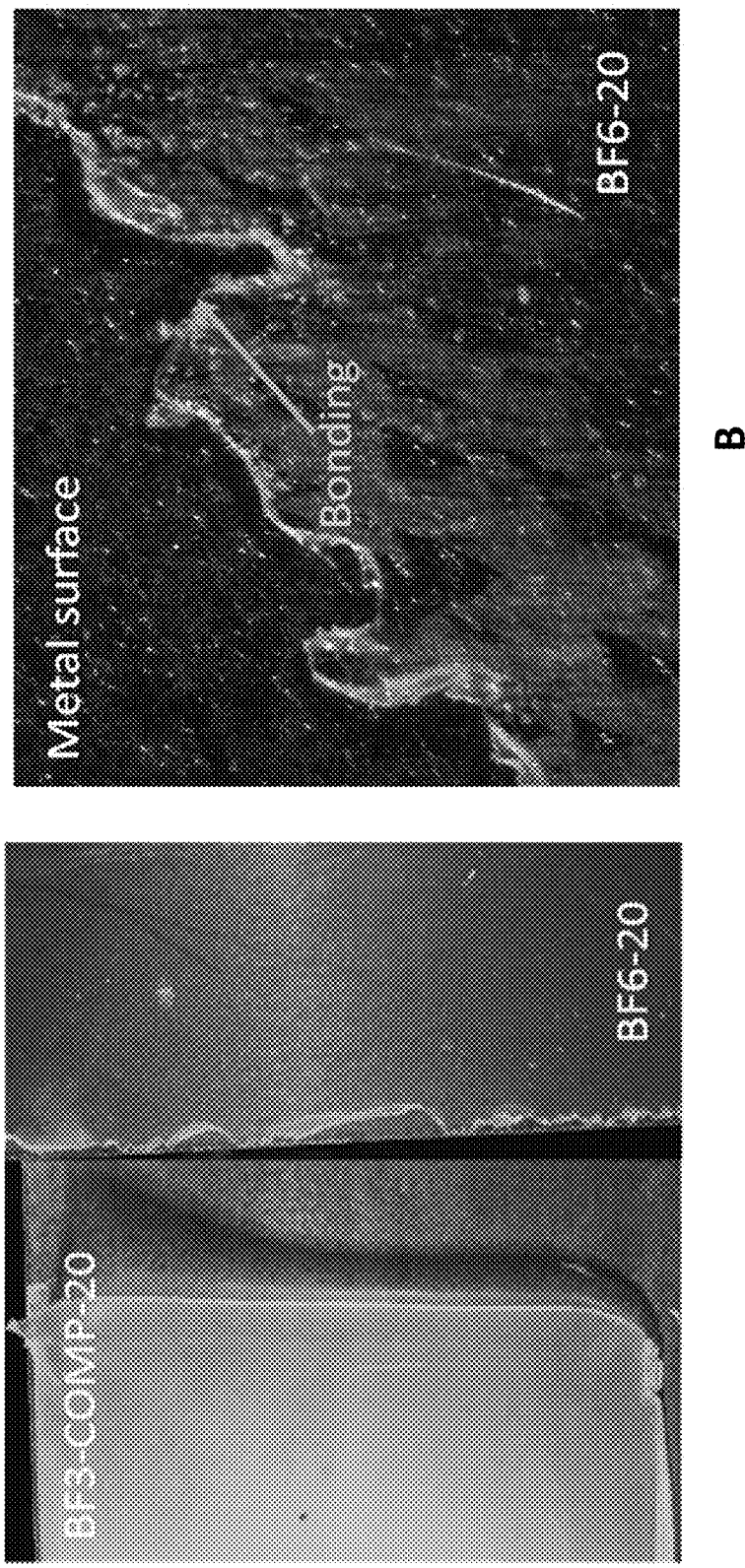
FIG. 12 (A, B) provides optical microscopy images of adhesive and solvent free polymer bonding on steel surfaces.

Optical microscopy images of adhesive and solvent free polymer bonding on steel surfaces are provided in FIG. 12 (A, B).

Figure 13:
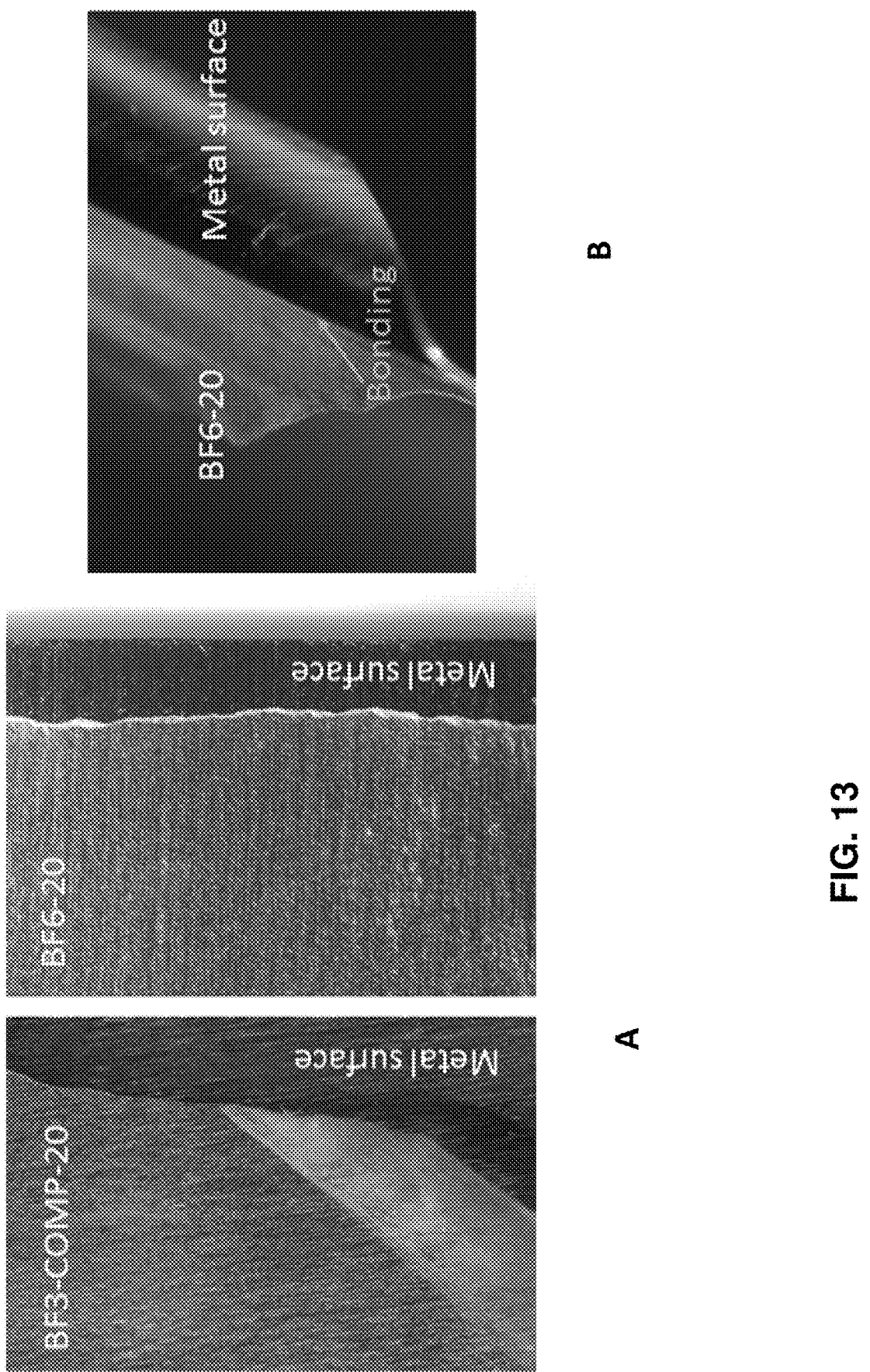
FIG. 13 (A, B) provides optical microscopy images of adhesive and solvent free polymer bonding on aluminum surfaces.

Optical microscopy images of adhesive and solvent free polymer bonding on aluminum surfaces are provided in FIG. 13 (A, B).

FIG. 12 (A) and FIG. 13 (A) show side-by-side comparison of melt adhesion of BF3-COMP-20 and BF6-20 samples on the steel and aluminum surfaces, respectively. From both A figures it can be seen that BF3-COMP-20 polymer films have poor bonding with either metal substrates while BF6-20 samples display improved bonding. Peeled corners of the BF3-COMP-20 films are obvious from the optical microscopy images. FIG. 12 (B) and FIG. 13 (B) show interaction of the BF6-20 polymer films with the steel and aluminum substrates, respectively.

Example 7

Blends of PP and amphiphilic graft copolymers and comparative formulations according to Table 1 were prepared in a pellet form at 220° C. using a Rheomex OS 16 mm twin screw extruder from Thermo Fisher Scientific. The blend compositions are provided in Table 8 of Example 3. Obtained pellets were used to prepare polymer specimens with 3.000 inches×0.600 inches dimensions and 0.063 inches thickness using Carver compression molding machine at 200° C. temperature.

Polycarbonate (PC) substrates to perform solvent bonding were rigid substrates having a material of Makrolon® 2558 resin with dimensions of 3.000 inches×0.600 inches and 0.063 inch thickness.

Example 8

Testing

Effects of amphiphilic graft copolymers on solvent bonding of flexible substrates onto polycarbonate (PC) substrates were analyzed. Solvent bonding on the PC substrates were performed using cyclohexanone as a bonding solvent and a curing (drying) time of 72 hours.

Melt Flow Rate (MFR).

ASTM 1238-13 method was used for melt flow rate (MFR) measurement at 230° C. using 2.16 kg weight.

Bonding Force Measurements.

Bonding force was measured using Instron 5965 with 5 kN load cell and tensile test fixture; test speed was 10 in/min.

Table 12 summarizes the melt adhesion results, where 10 specimens were tested for each sample and results were averaged.

TABLE 12

| Sample Name | Maximum Force (N) | Standard Deviation |
| --- | --- | --- |
| BF1-COMP-20 | 0 | 0 |
| BF2-COMP-20 | 0 | 0 |
| BF3-COMP-20 | 1.9 | 6.5 |
| BF4-COMP-20 | 3.6 | 5.3 |
| BF5-20 | 95 | 4.8 |
| BF6-20 | 144 | 5.7 |
| BF7-20 | 141 | 6.0 |

Figure 14:
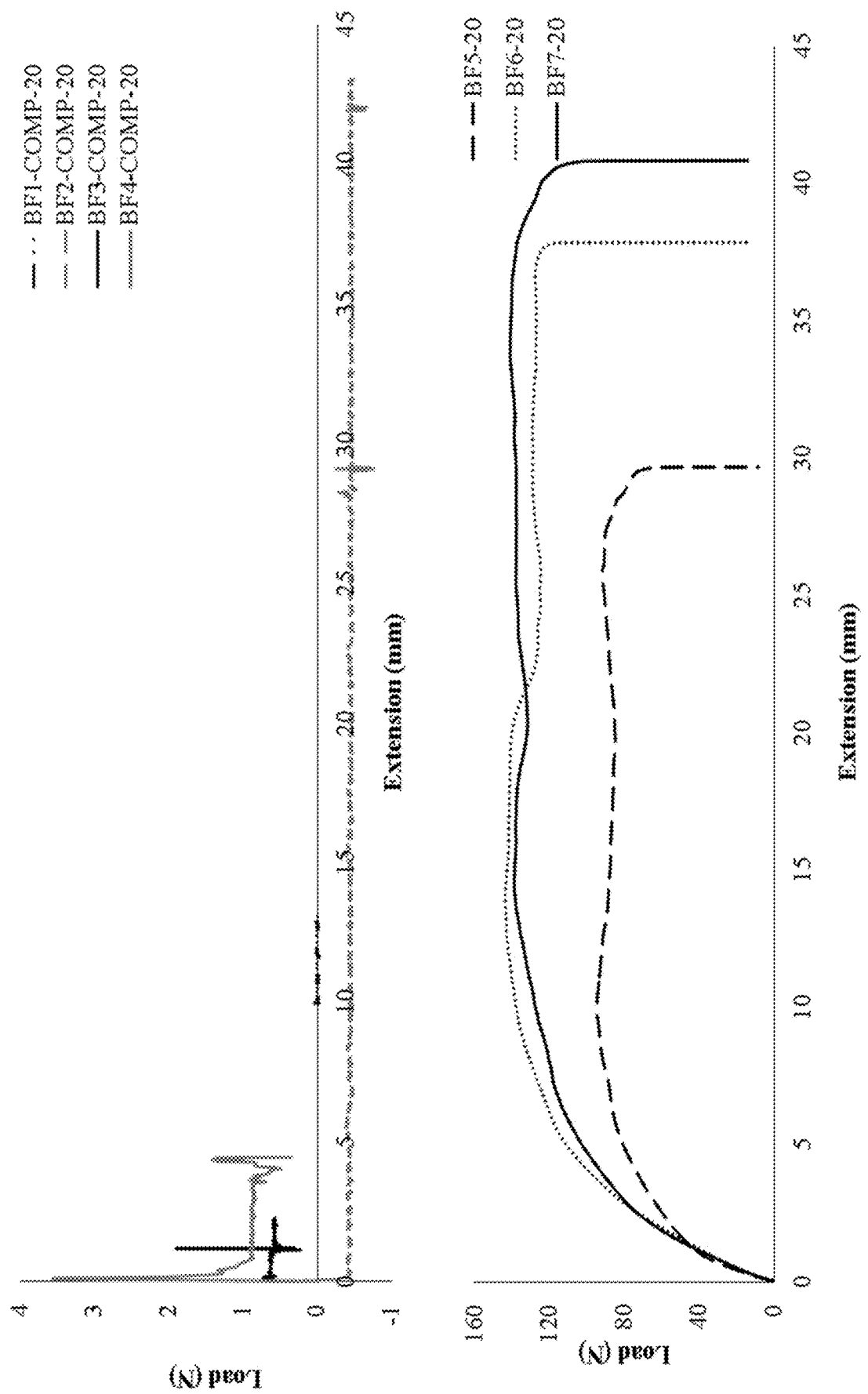
FIG. 14 provides graphs of load (N) versus extension (mm) for adhesion force measurements for polypropylene and amphiphilic graft copolymers compositions solvent-bonded to polycarbonate substrates.

FIG. 14 provides graphs of load (N) versus extension (mm), showing effects of 20 wt. % amphiphilic graft copolymer (BF5-20, BF6-20, -BF7-20) on the solvent bonding of PP on the PC substrate in comparison with PP performance with 20 wt. % comparative formulations (BF1-COMP-20, BF2-COMP-20, BF3-COMP-20, -BF4-COMP-20,). As seen from the graphs amphiphilic graft copolymers improves solvent bonding of PP on the PC surface which subsequently result higher maximum and averaged debonding forces across the PC substrate than PP samples with 20 wt. % comparative formulations.

Example 9

Testing

Effects of concentration of amphiphilic graft copolymers (wt. %) on melt adhesion of flexible substrates onto polycarbonate (PC) substrates were analyzed. The blend compositions are provided in Table 10, where Formulation 6 of Table 1 was used.

Melt adhesion was measured as discussed in Example 4. Table 13 summarizes the melt adhesion results, where 10 specimens were tested for each sample and results were averaged.

TABLE 13

| Sample Name | Maximum Force (N) | Standard Deviation |
| --- | --- | --- |
| BF6-0 | 0.3 | 3.5 |
| BF6-0.5 | 42 | 4.8 |
| BF6-1 | 78 | 5.7 |
| BF6-5 | 95 | 5.0 |
| BF6-10 | 120 | 4.7 |
| BF6-20 | 144 | 5.5 |

Figure 15:
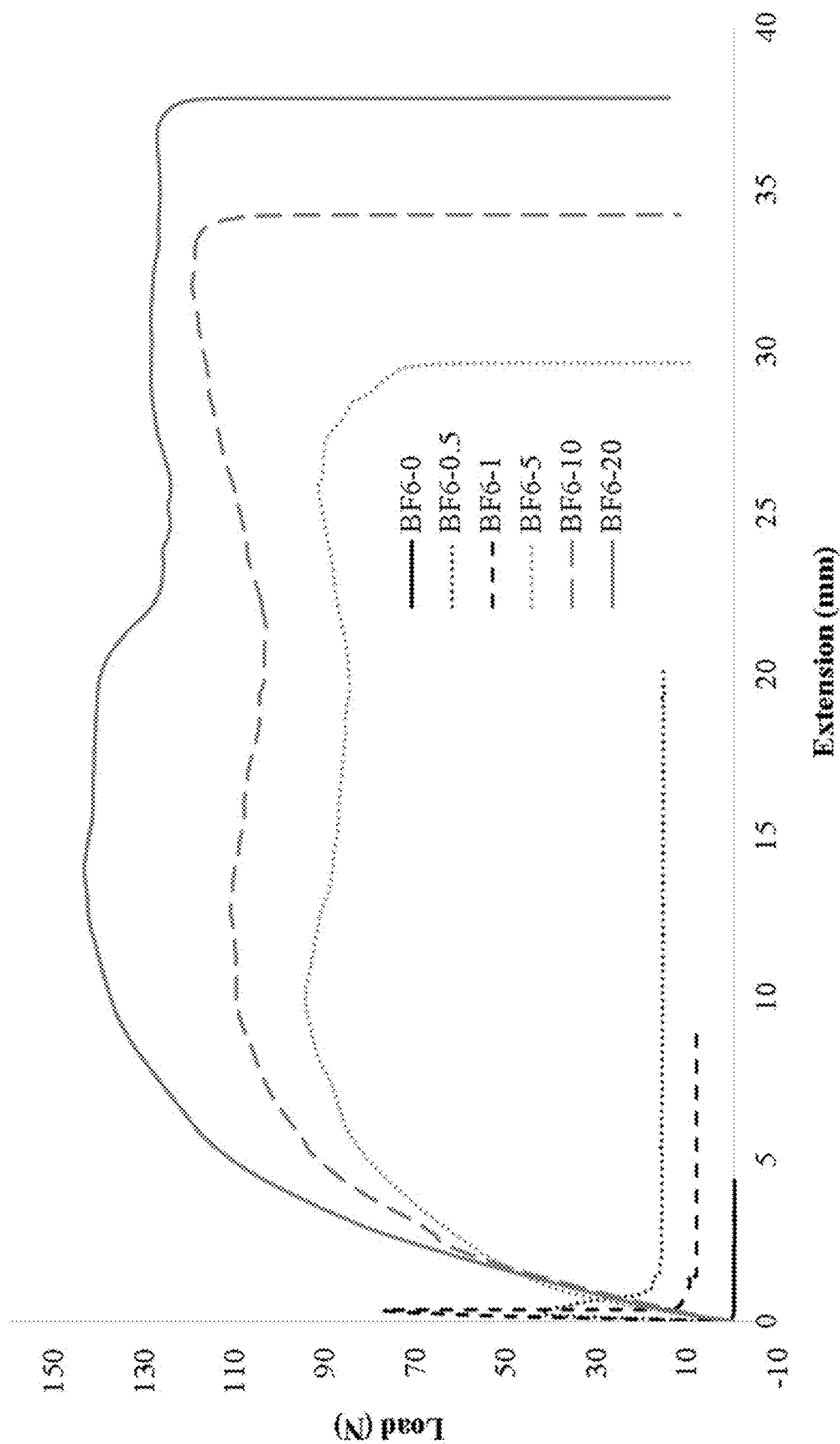
FIG. 15 provides graphs of load (N) versus extension (mm) for adhesion force measurements for polypropylene and amphiphilic graft copolymers compositions solvent-bonded to polycarbonate substrates.

FIG. 15 is a graph of load (N) versus extension (mm), showing effects of amphiphilic graft copolymer concentration on the solvent bonding behavior of PP across PC substrate. Amphiphilic graft copolymer improves solvent bonding of PP on the PC surface even at low 0.5 wt. % concentration level.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. An amphiphilic copolymer comprising a polypropylene backbone and an inorganic-organic hybrid side-chain grafted to the polypropylene backbone, the amphiphilic copolymer, which is according to Formula (I):

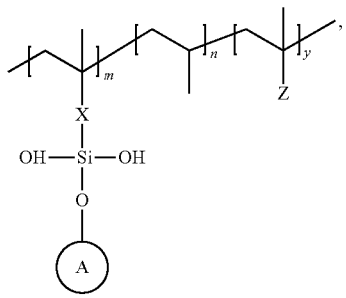

wherein X is an organic or an organo-functional group containing 1 to 6 carbons; A is selected from the group consisting of: silicon (Si), aluminum (Al), iron (Fe), titanium (Ti), silver (Ag), zinc (Zn), nickel (Ni), calcium (Ca), copper (Cu), tin (Sn), oxides thereof, hydroxides thereof, and mixtures of the foregoing; and n is in the range of about 78 to 99.9 mole percent; m is in the range of about 0.1 to 20 mole percent; the molar value of "y" is in the range of about 0 to 2.0 mole percent; and "Z", when y is greater than 0, comprises: —X$_2$-M; —XSi(OR)$_2$; or —XSi(OH)$_3$, wherein "-M-X$_2$" is an organo-metal salt and M is a metal selected from the group consisting of Na, Ca, Mg, Zn, Al and Fe (III) and X$_2$ is derived from a compound selected from the group consisting of: epoxy, amino, acrylate, methacryloxy, and vinyl, and "OR" is an alkoxy group having 1 to 4 carbons; and the amphiphilic copolymer has a long chain branching frequency in the range of 0.007 to 0.017 per 1000 carbon.

2. The amphiphilic copolymer of claim 1, wherein the inorganic-organic hybrid side-chain is a reaction product of an organo-silane and an inorganic oxide and/or hydroxide.

3. The amphiphilic copolymer of claim 1, wherein X is derived from a compound selected from the group consisting of epoxy, amino, acrylate, methacryloxy, and vinyl; and A is silica or aluminum oxyhydroxide.

4. The amphiphilic copolymer of claim 1, wherein the inorganic-organic hybrid side-chain is a reaction product of an organo-functional silane and an inorganic oxide and/or hydroxide in solution, wherein a weight ratio of the organo-functional silane to the inorganic oxide and/or hydroxide is at least 10:1.

5. The amphiphilic copolymer of claim 1, wherein y is 0, and the amphiphilic copolymer is according to Formula (IA):

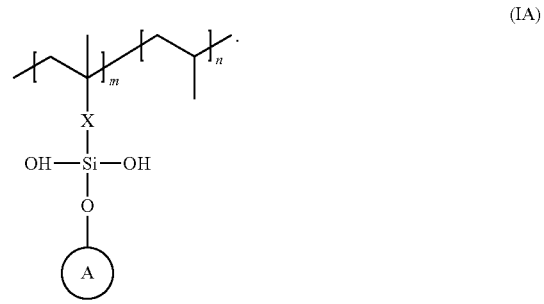

6. The amphiphilic copolymer of claim 5, wherein —XSi(OH)$_2$O is derived from 3-(trimethoxysilyl)propyl methacrylate.

7. The amphiphilic copolymer of claim 6, wherein A is derived from Si(OH)$_4$ or SiO$_2$.

8. The amphiphilic copolymer of claim 1 having a melting point in the range of 140 to 180° C.

9. The amphiphilic copolymer of claim 1 having a capillary viscosity in the range of 100 to 300 Pa·s at 180 s$^{-1}$.

10. The amphiphilic copolymer of claim 1 having a weight average molecular weight (Mw) in the range of about 100,000 to about 350,000 g/mol.

11. The amphiphilic copolymer of claim 1 having a dispersity index in the range of 1.5 to 9.

12. The amphiphilic copolymer of claim 1 having a melt flow rate in the range of 15 to 55 g/10 minutes.

13. A medical device formed from a blend comprising:
a base polymeric formulation comprising at least a homopolymer or co-polymer of propylene; and
an additive comprising a copolymer (PP-g-XSiOA) comprising a polypropylene backbone and an inorganic-organic hybrid side-chain grafted to the polypropylene backbone, the amphiphilic copolymer, which is according to Formula (I):

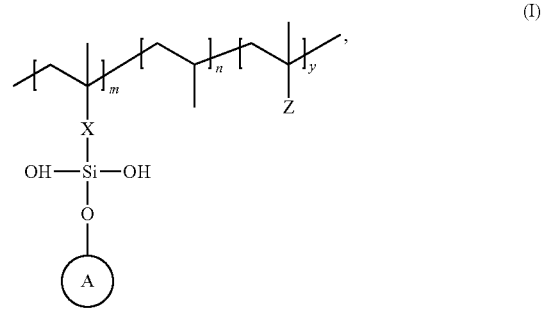

where "X" is an organic group or an organo-functional group containing 1 to 6 carbons; "A" is selected from the group consisting of: silicon (Si), aluminum (Al), iron (Fe), titanium (Ti), silver (Ag), zinc (Zn), nickel (Ni), calcium (Ca), copper (Cu), tin (Sn), oxides thereof, hydroxides thereof, and mixtures of the foregoing; and n is in the range of about 78 to 99.9 mole percent; m is in the range of about 0.1 to 20 mole percent; the molar value of "y" is in the range of about 0 to 2.0 mole percent; and "Z", when y is greater than 0, comprises: —X$_2$-M; —XSi(OR)$_3$; or —XSi(OH)$_3$, wherein "-M-X$_2$" is an organo-metal salt and M is a metal selected from the group consisting of Na, Ca, Mg, Zn, Al and Fe (III) and X$_2$ is derived from a compound selected from the group consisting of: epoxy, amino, acrylate, methacryloxy, and vinyl, and "OR" is an alkoxy group having 1 to 4 carbons; and wherein the copolymer (PP-g-XSiOA) has a long chain branching frequency in the range of 0.007 to 0.017 per 1000 carbon;

the PP-g-XSiOA being present in the blend in a range of about 0.01 to about 20.0% by weight of the blend.

14. The medical device of claim 13, wherein the base polymeric formulation comprises polypropylene homopolymer, a polyethylene-polypropylene co-polymer, a polypropylene-containing thermoplastic elastomer (TPE), or combinations thereof.

15. The medical device of claim 13, wherein X of the PP-g-XSiOA is derived from a compound selected from the group consisting of epoxy, amino, acrylate, methacryloxy, and vinyl; and A is silica or aluminum oxyhydroxide.

16. The medical device of claim 13, which has one or more improved characteristics relative to a comparative base polymeric formulation comprising at least a homopolymer or co-polymer of propylene without a PP-g-XSiOA additive, the improved characteristic being selected from the group consisting of: laser printability and/or marking; solvent bonding, and melt adhesion to polar surfaces.

17. The medical device of claim 13 which is in the form of tubing.

18. A medical device comprising:
a tubing comprising a polymeric blend comprising a base polymeric formulation comprising at least a homopolymer or co-polymer of propylene, and an additive comprising a copolymer (PP-g-XSiOA) comprising a polypropylene backbone and an inorganic-organic hybrid side-chain grafted to the polypropylene backbone, the amphiphilic copolymer, which is according to Formula (I):

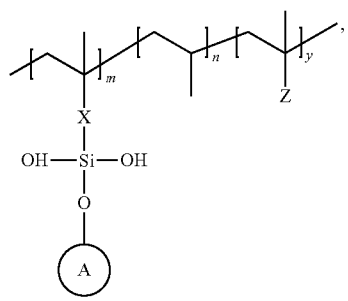

(I)

where "X" is an organic group or an organo-functional group containing 1 to 6 carbons; "A" is selected from the group consisting of: silicon (Si), aluminum (Al), iron (Fe), titanium (Ti), silver (Ag), zinc (Zn), nickel (Ni), calcium (Ca), copper (Cu), tin (Sn), oxides thereof, hydroxides thereof, and mixtures of the foregoing; and n is in the range of about 78 to 99.9 mole percent; m is in the range of about 0.1 to 20 mole percent; the molar value of "y" is in the range of about 0 to 2.0 mole percent; and "Z", when y is greater than 0, comprises: —X$_2$-M; —XSi(OR)$_3$; or —XSi(OH)$_3$, wherein "-M-X$_2$" is an organo-metal salt and M is a metal selected from the group consisting of Na, Ca, Mg, Zn, Al and Fe (III) and X$_2$ is derived from a compound selected from the group consisting of: epoxy, amino, acrylate, methacryloxy, and vinyl, and "OR" is an alkoxy group having 1 to 4 carbons; and wherein the copolymer (PP-g-XSiOA) has a long chain branching frequency in the range of 0.007 to 0.017 per 1000 carbon;

wherein the PP-g-XSiOA is present in the blend in an amount in the range of about 0.01 to about 20.0% by weight of the blend; and a connector bonded to the tubing.

19. The medical device of claim 18, wherein the base polymeric formulation comprises polypropylene homopolymer, a polyethylene-polypropylene co-polymer, a polypropylene-containing thermoplastic elastomer (TPE), or combinations thereof.

20. The medical device of claim 18, wherein X of the PP-g-XSiOA is derived from a compound selected from the group consisting of: epoxy, amino, acrylate, methacryloxy, and vinyl; and A is silica or aluminum oxyhydroxide.

21. The medical device of claim 18, wherein the connector comprises a metal.

22. The medical device of claim 21, wherein the metal is selected from the group consisting of: steel, cobalt, titanium, tantalum, and their alloys.

23. The medical device of claim 21, wherein the connector is melt-bonded to the tubing.

24. The medical device of claim 18, wherein the connector comprises a polar material.

25. The medical device of claim 24, wherein the polar material is selected from the group consisting of: poly (methyl methacrylate) (PMMA), styrene maleic anhydride (SMA), polycarbonate (PC), and methyl methacrylate-acrylonitrile-butadiene-styrene (MABS).

26. The medical device of claim 24, wherein the connector is solvent-bonded to the tubing.

27. A method of making a medical device comprising:
obtaining a copolymer (PP-g-XSiOA) comprising a polypropylene backbone and an inorganic-organic hybrid side-chain grafted to the polypropylene backbone, the amphiphilic copolymer, which is according to Formula (I):

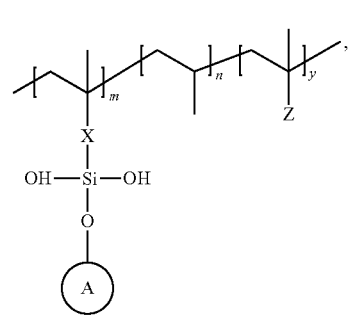

(I)

where "X" is an organic group or an organo-functional group containing 1 to 6 carbons; "A" is selected from the group consisting of: silicon (Si), aluminum (Al), iron (Fe), titanium (Ti), silver (Ag), zinc (Zn), nickel (Ni), calcium (Ca), copper (Cu), tin (Sn), oxides thereof, hydroxides thereof, and mixtures of the foregoing; and "Z", when y is greater than 0, comprises: —$X_2$-M; —$XSi(OR)_3$; or —$XSi(OH)_3$, wherein "-M-$X_2$" is an organo-metal salt and M is a metal selected from the group consisting of Na, Ca, Mg, Zn, Al and Fe (III) and $X_2$ is derived from a compound selected from the group consisting of: epoxy, amino, acrylate, methacryloxy, and vinyl, and "OR" is an alkoxy group having 1 to 4 carbons; and wherein the copolymer (PP-g-XSiOA) has a long chain branching frequency in the range of 0.007 to 0.017 per 1000 carbon;

combining the PP-g-XSiOA with a base polymeric formulation comprising at least a homopolymer or copolymer of propylene to form a blend, the PP-g-XSiOA being present in the blend in a range of about 0.01 to about 20.0% by weight of the blend;

forming a tubing from the blend; and bonding the tubing to a connector in the absence of an adhesive to form the medical device.

28. The method of claim 27, wherein the connector comprises a metal.

29. The method of claim 28, wherein the metal is selected from the group consisting of: steel, cobalt, titanium, tantalum, and their alloys.

30. The method of claim 28, wherein the connector is melt-bonded to the tubing.

31. The method of claim 27, wherein the connector comprises a polar material.

32. The method of claim 31, wherein the polar material is selected from the group consisting of: poly(methyl methacrylate) (PMMA), styrene maleic anhydride (SMA), polycarbonate (PC), and methyl methacrylate-acrylonitrile-butadiene-styrene (MABS).

33. The method of claim 31, wherein the connector is solvent-bonded to the tubing.

* * * * *